(12) United States Patent
Goldan et al.

(10) Patent No.: US 11,789,167 B2
(45) Date of Patent: Oct. 17, 2023

(54) HIGH RESOLUTION DEPTH-ENCODING PET DETECTOR WITH PRISMATOID LIGHT GUIDE ARRAY

(71) Applicant: THE RESEARCH FOUNDATION FOR THE STATE UNIVERSITY OF NEW YORK, Albany, NY (US)

(72) Inventors: Amirhossein Goldan, Stony Brook, NY (US); Andrew Labella, New Rochelle, NY (US); Wei Zhao, East Setauket, NY (US); Anthony R. Lubinsky, Port Jefferson Station, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/727,995

(22) Filed: Apr. 25, 2022

(65) Prior Publication Data

US 2022/0244411 A1  Aug. 4, 2022

Related U.S. Application Data

(63) Continuation of application No. 16/899,636, filed on Jun. 12, 2020, now Pat. No. 11,454,730, which is a
(Continued)

(51) Int. Cl.
*G01T 1/20* (2006.01)
*G01T 1/202* (2006.01)
(Continued)

(52) U.S. Cl.
CPC ............ *G01T 1/202* (2013.01); *G01T 1/1641* (2013.01); *G01T 1/2002* (2013.01); *G01T 1/29* (2013.01)

(58) Field of Classification Search
CPC ..... G01T 1/202; G01T 1/1641; G01T 1/2002; G01T 1/29; G01T 1/1642; G01T 1/2985;
(Continued)

(56) References Cited

U.S. PATENT DOCUMENTS

| 4,037,105 A | 7/1977 | Laurer |
| 4,531,058 A | 7/1985 | Burnham et al. |

(Continued)

FOREIGN PATENT DOCUMENTS

| CN | 1813202 A | 8/2006 |
| CN | 102626316 A | 8/2012 |

(Continued)

OTHER PUBLICATIONS

Muller et al., "Gradient tree boosting-based positioning method for monolithic scintillator crystals in positron emission tomography," IEEE Transactions on Radiation and Plasma medical sciences, vol. 2, No. 5, pp. 411-421. (Year: 2018).*

(Continued)

*Primary Examiner* — Kiho Kim
(74) *Attorney, Agent, or Firm* — Scully, Scott, Murphy & Presser, P.C.

(57) ABSTRACT

Provided is a particle detection device and method of fabrication thereof. The particle detection device includes a scintillator array that includes a plurality of scintillator crystals; a plurality of detectors provided on a bottom end of the scintillator array; and a plurality of prismatoids provided on a top end of the scintillator array. Prismatoids of the plurality of prismatoids are configured to redirect particles between top ends of crystals of the scintillator array. Bottom ends of a first group of crystals of the scintillator array are configured to direct particles to a first detector of the plurality of detectors and bottom ends of a second group of crystals of the scintillator array are configured to direct
(Continued)

particles to a second detector substantially adjacent to the first detector.

9 Claims, 28 Drawing Sheets

Related U.S. Application Data continuation of application No. PCT/US2020/018309, filed on Feb. 14, 2020.

(60) Provisional application No. 62/915,676, filed on Oct. 16, 2019, provisional application No. 62/806,035, filed on Feb. 15, 2019.

(51) Int. Cl.
*G01T 1/164* (2006.01)
*G01T 1/29* (2006.01)

(58) Field of Classification Search
CPC ... A61B 6/4208; A61B 6/4225; A61B 6/4258; A61B 6/4266; A61B 6/037
See application file for complete search history.

(56) References Cited

U.S. PATENT DOCUMENTS

| | | |
|---|---|---|
| 4,749,863 A | 6/1988 | Casey et al. |
| 4,750,972 A | 6/1988 | Casey et al. |
| 5,122,667 A | 6/1992 | Thompson |
| 5,453,623 A | 9/1995 | Wong et al. |
| 5,600,144 A | 2/1997 | Worstell |
| 6,087,663 A | 7/2000 | Moisan et al. |
| 6,114,703 A | 9/2000 | Levin et al. |
| 6,124,595 A | 9/2000 | Engdahl et al. |
| 6,346,706 B1 | 2/2002 | Rogers et al. |
| 6,362,479 B1 | 3/2002 | Andreaco et al. |
| 6,459,085 B1 | 10/2002 | Chang et al. |
| 6,909,097 B2 | 6/2005 | Schreiner et al. |
| 7,049,600 B2 | 5/2006 | Levin |
| 7,088,901 B2 | 8/2006 | Kim et al. |
| 7,164,136 B2 | 1/2007 | Aykac et al. |
| 7,180,074 B1 | 2/2007 | Crosetto |
| 7,291,841 B2 | 11/2007 | Nelson et al. |
| 7,304,309 B2 | 12/2007 | Suhami |
| 7,566,879 B2 | 7/2009 | Tümer |
| 7,692,156 B1 | 4/2010 | Nagarkar |
| 7,800,070 B2 | 9/2010 | Weinberg et al. |
| 7,956,331 B2 | 6/2011 | Lewellen et al. |
| 8,269,177 B2 | 9/2012 | Kim et al. |
| 8,294,110 B2 | 10/2012 | Burr |
| 8,450,692 B2 | 5/2013 | Siegel et al. |
| 8,476,593 B2 | 7/2013 | Degenhardt et al. |
| 8,937,285 B2 | 1/2015 | Kim et al. |
| 9,040,924 B2 | 5/2015 | Lewellen et al. |
| 9,194,959 B2 | 11/2015 | Schmand et al. |
| 9,304,211 B2 | 4/2016 | Goertzen |
| 9,442,199 B1 | 9/2016 | Oleinik et al. |
| 9,575,191 B1 | 2/2017 | Ng et al. |
| 9,606,245 B1 | 3/2017 | Czarnecki et al. |
| 9,915,739 B2 | 3/2018 | Baviera et al. |
| 10,054,697 B1 | 8/2018 | Vencelj et al. |
| 10,067,245 B2 | 9/2018 | Li et al. |
| 10,203,419 B2 | 2/2019 | Frazao et al. |
| 10,234,572 B2 | 3/2019 | Hadjioannou et al. |
| 10,310,098 B1 | 6/2019 | Qiang et al. |
| 10,379,228 B2 | 8/2019 | Sowards-Emmerd et al. |
| 10,962,661 B2 | 3/2021 | Li et al. |
| 2004/0195512 A1 | 10/2004 | Crosetto |
| 2004/0227091 A1 | 11/2004 | LeBlanc et al. |
| 2005/0006589 A1 | 1/2005 | Joung et al. |
| 2005/0023474 A1 | 2/2005 | Persyk et al. |
| 2005/0031293 A1 | 2/2005 | Kim et al. |
| 2005/0253073 A1 | 11/2005 | Joram et al. |
| 2006/0284094 A1 | 12/2006 | Inbar |
| 2008/0156993 A1 | 7/2008 | Weinberg et al. |
| 2010/0012846 A1 | 1/2010 | Wang |
| 2010/0168947 A1 | 7/2010 | Winso et al. |
| 2010/0294940 A1 | 11/2010 | Wieczorek |
| 2012/0061577 A1 | 3/2012 | Oleinik et al. |
| 2012/0068076 A1 | 3/2012 | Daghighian |
| 2012/0085913 A1 | 4/2012 | McCroskey et al. |
| 2012/0181436 A1 | 7/2012 | Mollov |
| 2013/0193330 A1 | 8/2013 | Wagadarikar et al. |
| 2013/0334428 A1 | 12/2013 | Kim et al. |
| 2015/0001403 A1 | 1/2015 | Kim et al. |
| 2016/0223690 A1 | 8/2016 | Uchida |
| 2016/0320496 A1 | 11/2016 | Frach et al. |
| 2018/0038968 A1 | 2/2018 | Frisch et al. |
| 2018/0252825 A1 | 9/2018 | Baviera et al. |
| 2019/0242835 A1 | 8/2019 | Roy |
| 2019/0353807 A1 | 11/2019 | Furenlid et al. |
| 2022/0120923 A1 | 4/2022 | Goldan et al. |

FOREIGN PATENT DOCUMENTS

| | | |
|---|---|---|
| CN | 105452902 B | 2/2019 |
| CN | 107110980 B | 5/2020 |
| CN | 111366969 A | 7/2020 |
| CN | 211905711 U | 11/2020 |
| DE | 69837429 T2 | 12/2007 |
| EP | 0813692 B1 | 8/2002 |
| EP | 1627239 B1 | 10/2006 |
| EP | 1877831 B1 | 12/2011 |
| EP | 1328189 B1 | 8/2016 |
| EP | 3207406 B1 | 7/2020 |
| EP | 3862794 A1 | 8/2021 |
| EP | 3871605 A1 | 9/2021 |
| JP | 2004512502 A | 4/2004 |
| JP | 5771197 B2 | 8/2015 |
| JP | 2017538132 A | 12/2017 |
| JP | 2018044961 A | 3/2018 |
| JP | 2020003488 A | 1/2020 |
| JP | 2020060545 A | 4/2020 |
| JP | 2020197523 A | 12/2020 |
| KR | 101586973 B1 | 1/2016 |
| KR | 20210102987 A | 8/2021 |
| WO | 8603596 A1 | 6/1986 |
| WO | 2014064295 A1 | 5/2014 |
| WO | 2016/062799 A1 | 4/2016 |
| WO | 2016077479 A1 | 5/2016 |
| WO | 2019177461 A1 | 9/2019 |
| WO | 2020168205 A9 | 8/2020 |
| WO | 2021115917 A1 | 6/2021 |
| WO | 2021146559 A1 | 7/2021 |
| WO | 2021173708 A1 | 9/2021 |
| WO | 2021209501 A1 | 10/2021 |
| WO | 2022051579 A1 | 3/2022 |
| WO | 2022076643 A1 | 4/2022 |

OTHER PUBLICATIONS

LaBella, A. et al., "Prism Mirror Light Guide for Enhanced Gamma Ray Localization in PET", 2019 IEEE Nuclear Science Symposium and Medical Imaging Conference (NSS/MIC), 2019, pp. 1-4.

Supplementary European Search Report dated Sep. 15, 2022 received in European Patent Application No. 20732092.0.

Nagadarikar, A. et al., "Sensitivity Improvement of Time-of-Flight (ToF) PET Detector Through Recovery of Compton Scattered Annihilation Photons", IEEE Transactions on Nuclear Science, Feb. 2014, pp. 121-125, vol. 61, No. 1.

Cabello, J. et al., "Position Reconstruction in Detectors Based on Continuous Crystals Coupled to Silicon Photomultiplier Arrays", 2011 IEEE Nuclear Science Symposium Conference Record, Oct. 2011, pp. 3911-3916.

Extended European Search Report dated Nov. 9, 2022 received in European Patent Application No. 20732092.0.

PCT/ISA/210 Search Report issued on PCT/US2020/018309, dated Jun. 16, 2020, pp. 3.

PCT/ISA/237 Written Opinion issued on PCT/US2020/018309, dated Jun. 16, 2020, pp. 7.

(56) References Cited

OTHER PUBLICATIONS

Office Action dated Jun. 14, 2021 received in U.S. Appl. No. 16/899,636.
Notice of Allowance dated Jan. 20, 2022 received in U.S. Appl. No. 16/899,636.

* cited by examiner

US 11,789,167 B2

HIGH RESOLUTION DEPTH-ENCODING PET DETECTOR WITH PRISMATOID LIGHT GUIDE ARRAY

PRIORITY

This application is a continuation of U.S. application Ser. No. 16/899,636, filed with the U.S. Patent and Trademark Office on Jun. 12, 2020 which is a continuation of International Application No. PCT/US2020/018309, filed with the U.S. Patent and Trademark Office on Feb. 14, 2020, and claims benefit of U.S. Provisional Patent Applications Nos. 62/806,035 and 62/915,676 filed with the U.S. Patent and Trademark Office on Feb. 15, 2019 and Oct. 16, 2019, respectively, the entire contents of each which is incorporated herein by reference.

GOVERNMENT SUPPORT

This invention was made with government support under grant number EB024849 awarded by the National Institutes of Health. The government has certain rights in the invention.

BACKGROUND OF THE INVENTION

1. Field of the Invention

The present invention relates generally to the field of radiation imaging and, in particular, to positron emission tomography (PET).

2. Description of the Related Art

Molecular imaging with PET is a powerful technique used primarily for diagnosis, treatment selection, treatment monitoring and research in cancer [1] and neuropsychiatric disorders [2]. Despite its high molecular specificity, quantitative nature and clinical availability, PET has not been able to achieve its full potential as the go-to molecular imaging modality due in large part to its relatively poor spatial resolution, currently on the order of 3-6 mm [3,4]. With this kind of spatial resolution, it is not possible to measure target density in small nodules and in many human and rodent brain regions relevant to disease etiology and pathophysiology.

Depth-encoding PET detector modules have been developed to mitigate parallax error (mispositioning of the line of response) for long scintillator crystals [5]. This enables small diameter PET rings with reduced component cost per detector ring, large solid angle coverage for increased sensitivity, and reduced contribution of annihilation gamma ray acollinearity on spatial resolution when using crystals with small cross-sectional area [4,6]. In addition, depth-of-interaction (DOI) information can be used to deconvolve optical photon transport in long crystals, thus improving timing resolution [7,8]. Depth-encoding detectors based on dual-ended readout achieve the best continuous DOI resolution of <2 mm [9,10]. High resolution PET systems such as mammography dedicated Clear-PEM have been developed using dual-ended DOI readout detectors [11], but these systems are too costly to be commercialized due to the large number of readout electronics compared to standard single-ended readout PET scanners. A recently developed high resolution variant of these detectors shows relatively poor energy and timing resolutions due to the use of glass light guides at the crystal-readout interface, which are required to achieve accurate crystal identification [12]. Alternative single-ended readout detector modules have been proposed to obtain DOI information such as multi-layer phoswich blocks [13,14], retroreflectors for modules with monolithic scintillators [15], and other custom reflector designs [16,17]. However, in all these designs tradeoffs exists among depth-encoding, cost, scintillator-to-readout coupling ratio, crystal identification accuracy, energy resolution, and timing resolution. To mitigate these tradeoffs, an ideal depth-encoding detector module is one with single-ended readout where the crystal array is directly coupled to silicon photomultiplier (SiPM) pixels, without any intermediate glass light guide, to minimize sharing of downward traveling scintillation photons across multiple pixels and retain good timing resolution. In addition, upward traveling photons, which do not contribute to the timing information, should be redirected via 180° bending of their paths towards the nearest neighboring SiPMs to retain good energy and DOI resolutions and mimic the behavior of dual-ended depth-encoding readout detectors.

Accordingly, detector modules consisting of depolished multicrystal scintillator arrays coupled 4-to-1 to SiPM pixels on one side and a uniform glass light guide on the opposite side have recently been investigated in efforts to develop a practical and cost-effective high resolution time-of-flight (TOF) PET scanner, as well as achieve continuous DOI localization using single-ended readout [8,18,19]. See, U.S. Pat. No. 10,203,419 to Frazao et al., the contents of which are incorporated herein by reference. In these detector modules, energy weighted average method is utilized for crystal identification to achieve energy and DOI resolutions of 9% and 3 mm full width at half maximum (FWHM), respectively, using $1.53 \times 1.53 \times 15$ mm$^3$ crystals and $3 \times 3$ mm$^2$ SiPM pixels [8]. However, these arrays suffer from poor crystal identification along their edges and corners due to the lack of light sharing neighbors [19], an issue that must be addressed since the edge and corner pixels comprise 75% and 44% of 4×4 and 8×8 SiPM readout chips, respectively. Also, intercrystal light sharing is inefficient when using a uniform glass light guide since many upward traveling photons are reflected back into the primary column and the rest are isotropically shared with a Gaussian intensity distribution amongst neighbors. The problem with isotropic light sharing is the distribution of low-intensity signal across many SiPMs, the integrity of which will be severely affected by dark counts, resulting in degraded energy and DOI resolutions.

SUMMARY OF THE INVENTION

To overcome shortcomings of conventional systems, a particle detector and a method for operation of same are provided herein based on a prismatoid PET (Prism-PET) detector module.

Accordingly, aspects of the present invention address the above problems and disadvantages and provide the advantages described below. An aspect of the present invention provides a particle detection device that includes a scintillator array comprising a plurality of scintillator crystals, a plurality of detectors provided on a bottom end of the scintillator array, and a plurality of prismatoids provided on a top end of the scintillator array. Each prismatoid of the plurality of prismatoids is configured to redirect particles between top ends of crystals of the scintillator array. Bottom ends of a first group of crystals of the scintillator array are configured to direct particles to a first detector of the plurality of detectors, and bottom ends of a second group of crystals of the scintillator array are configured to direct particles to a second detector substantially adjacent to the first detector.

An aspect of the present disclosure provides a particle detector that includes a scintillator array comprising a plurality of scintillator crystals, a plurality of detectors provided on a bottom end of the scintillator array, a plurality of prismatoids provided on a top end of the scintillator array, and at least one processor in operative communication with the plurality of detectors. The at least one processor comprises a plurality of supervised machine learning algorithms configured to perform 3D gamma ray localization of at least one interaction site within at least one scintillator crystal of the plurality of scintillator crystals.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE INVENTION

The following detailed description of certain embodiments of the present invention will be made with reference to the accompanying drawings. In describing the invention, explanation about related functions or constructions known in the art are omitted for the sake of clearness in understanding the concept of the invention, to avoid obscuring the invention with unnecessary detail.

Disclosed herein are single-ended readout depth-encoding detector modules that utilize specialized patterns of segmented prismatoid light guides. Among the features of the Prism-PET detector modules disclosed in the various embodiments, at least three distinct prismatoid designs are utilized, i.e. a center prismatoid, an edge prismatoid, and a corner prismatoid, with each of the center prismatoid, the edge prismatoid, and the corner prismatoid being of different predefined design to mitigate edge and corner artifacts, thus achieving uniform crystal identification performance.

Intercrystal light sharing is confined to only crystals belonging to nearest SiPM neighbors to create a deterministic and anisotropic intercrystal light sharing pattern and maximize signal-to-background ratio on those SiPMs to improve both energy and DOI resolutions.

The segmentation pattern improves crystal identification by decoupling adjacent crystals that would otherwise have similar readout patterns, with the shape of each prismatoid being interchangeable, with embodiments of the prismatoid being substantially shaped as at least one of at least one prism, at least one antiprism, at least one frustum, at least one triangle, at least one cupola, at least one parallelepiped, at least one wedge, at least one pyramid, at least one truncated pyramid, at least one portion of a sphere, at least one cuboid, and at least one pyramid. For ease of reference, right triangular prisms are discussed herein, with the right triangular prisms enhancing intercrystal light sharing ratios, thus improving both crystal identification and DOI resolution.

When optical photons enter the hypotenuse of the right triangular prisms, the optical photons undergo 180° deviation, efficiently guiding them to neighboring crystals which are coupled to different readout pixels due to the offset crystal-to-prism coupling scheme with respect to crystal-to-pixel coupling, as illustrated in FIGS. 2 and 4-8.

Figure 1:
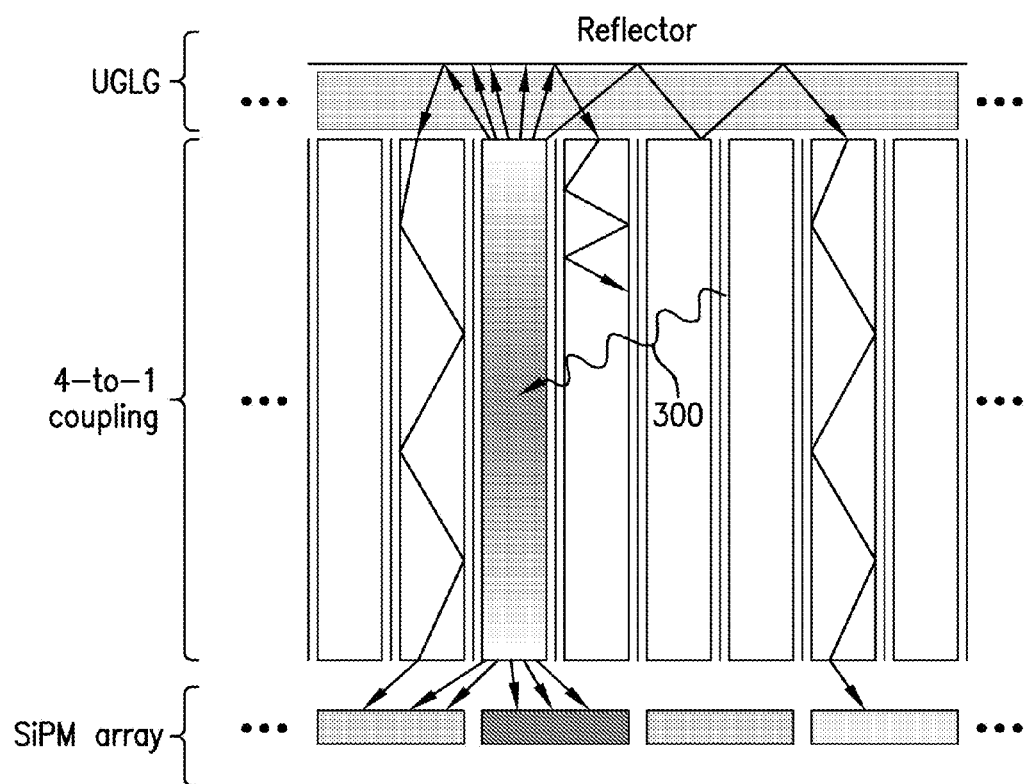
FIG. 1 illustrates a uniform glass light guide module and distribution of light using same in a known detection system.
Figure 2:
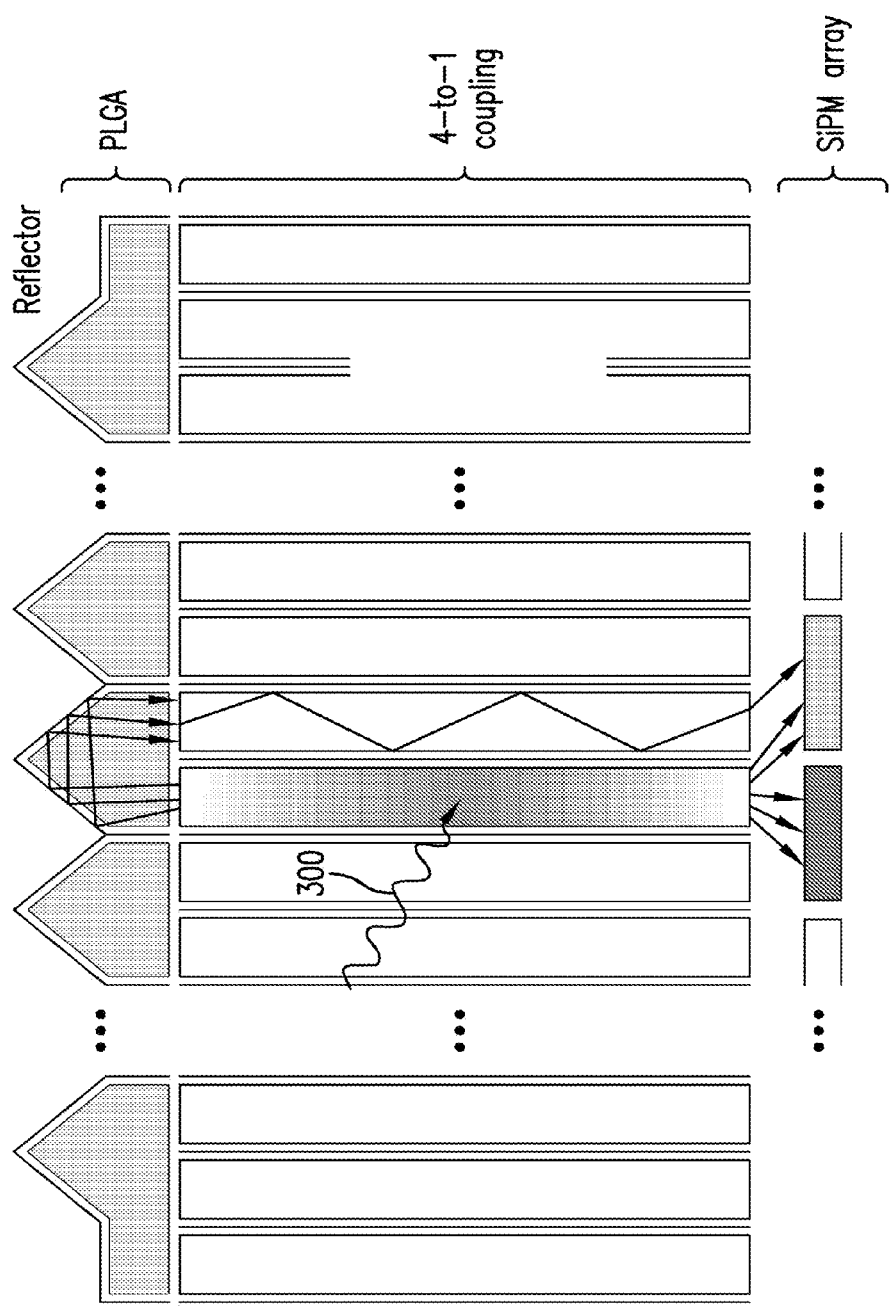
FIG. 2 illustrates detector modules with a specialized pattern of segmented prismatoid light guide according to embodiments of the present disclosure.
Figure 3:
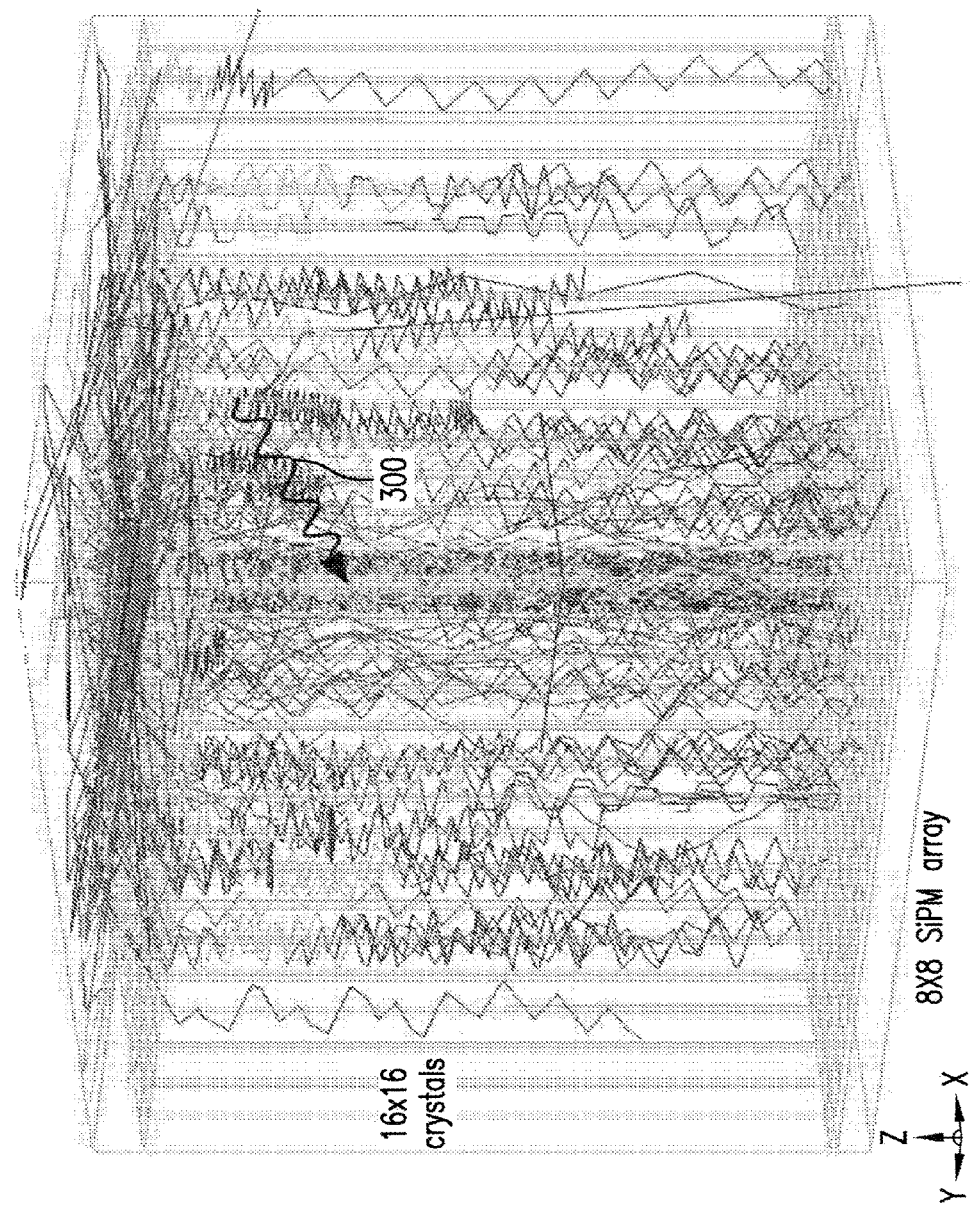
FIG. 3 illustrates distribution of light simulated in TracePro using the module illustrates in FIG. 1.

FIG. 1 illustrates a uniform glass light guide module of a known detector module and FIG. 3 illustrates the distribution of light using same, simulated in TracePro. FIG. 2 illustrates detector modules with a specialized pattern of segmented prismatoid light guide according to embodiments of the present disclosure.

Figure 4:
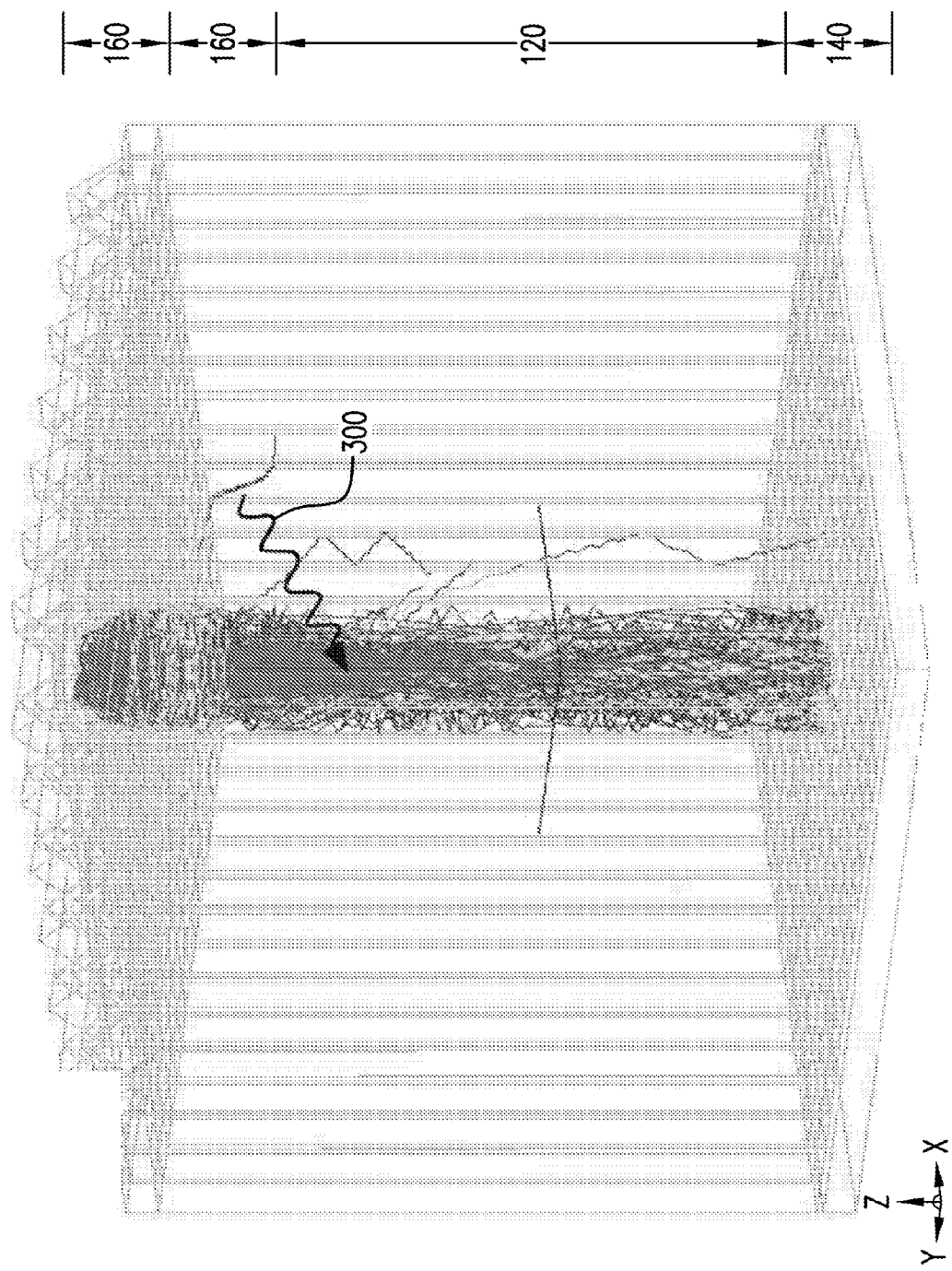
FIG. 4 illustrates distribution of light simulated in TracePro using the modules illustrated in FIG. 2 according to embodiments of the present disclosure.

FIG. 4, which illustrates the distribution of light using the detector modules in FIG. 2, simulated in TracePro, shows the confining light sharing to an array of 16×16 crystals 120 coupled to the same prismatoid, thereby enhancing intercrystal light sharing ratios, for the Prism-PET of embodiments of the present disclosure.

Figure 5:
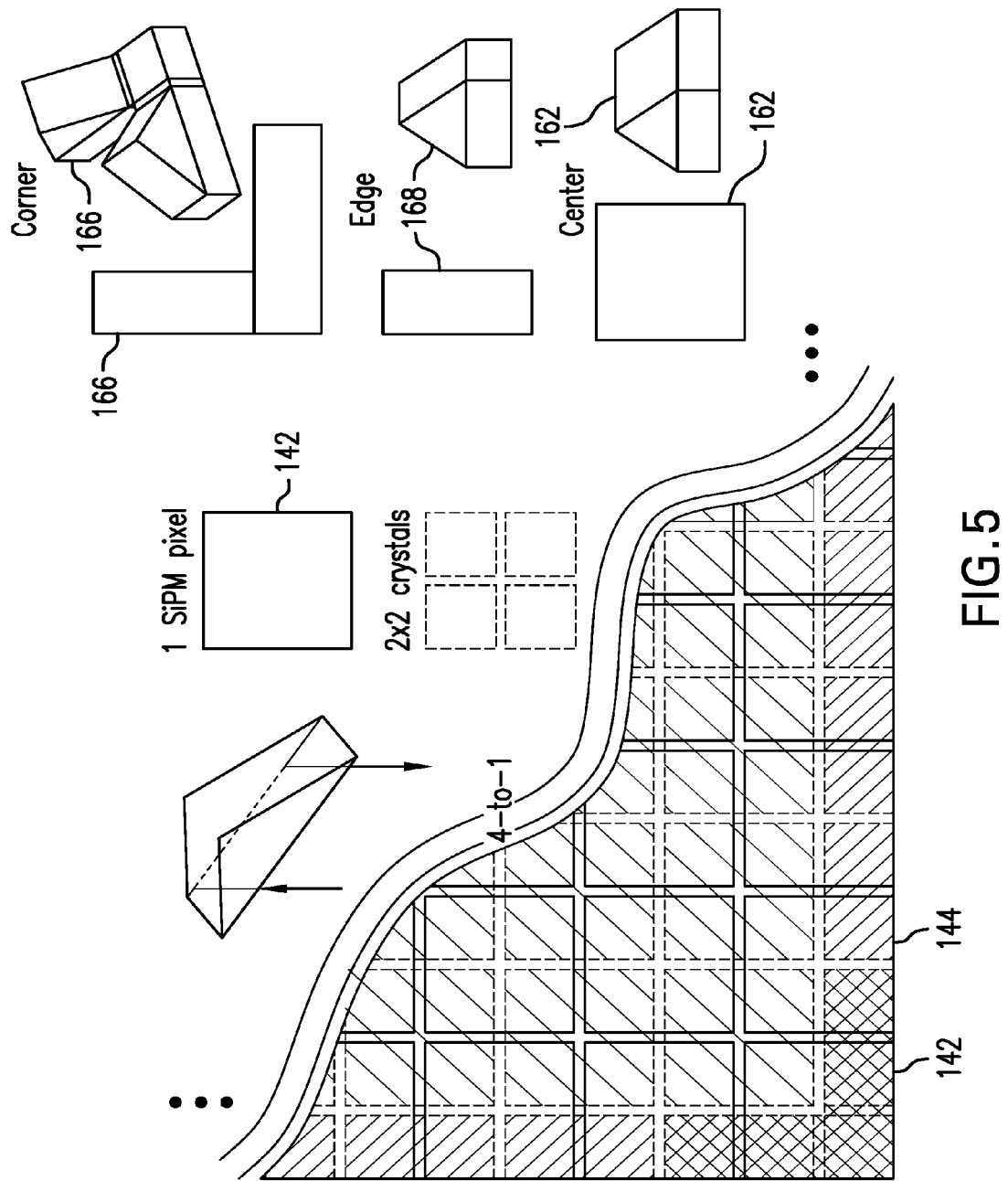
FIG. 5 illustrates arrangements of 4-to-1 coupled Prism-PET module according to embodiments of the present disclosure, FIG. 6 provides perspective views providing details of the prismatoid array, according to embodiments of the present disclosure.
Figure 6:
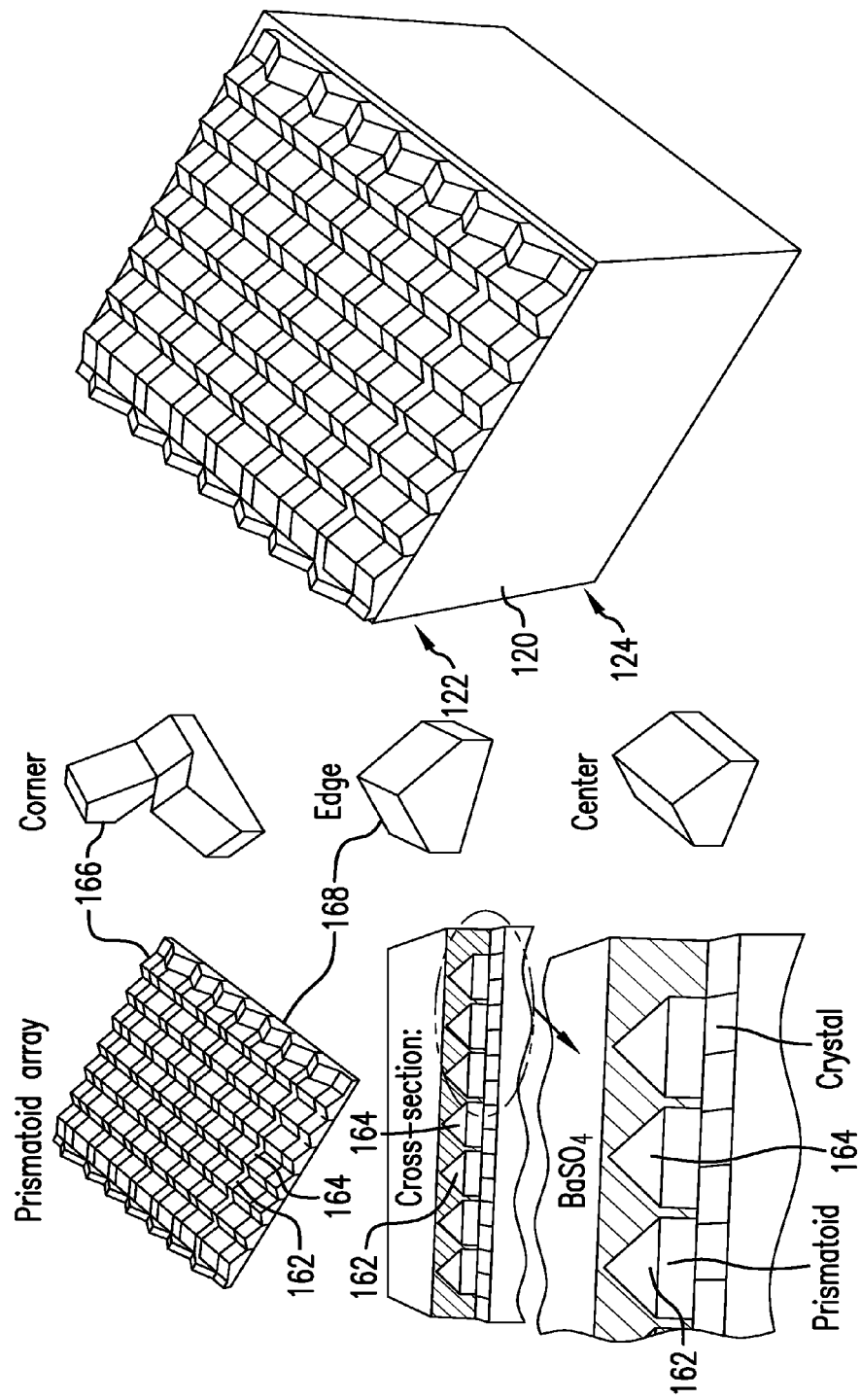

FIG. 5 illustrates arrangements of 4-to-1 coupled Prism-PET module according to embodiments of the present disclosure. The lower left corner of FIG. 5 is a plan view illustrating the relative arrangement of 2×2 crystals of a scintillator array comprising a plurality of scintillator crystals and SiPM pixels 140 of a plurality of detectors provided on a bottom end of the scintillator array. The upper right corner of FIG. 5 illustrates three distinct prismatoid designs being utilized in the embodiment of FIG. 5, with the center prismatoid 162, the edge prismatoid 168, and the corner prismatoid 166 having a different design for mitigating edge and corner artifacts, thus achieving uniform crystal identification performance. As illustrated in FIG. 6, the three distinct prismatoids are provided in a predefined arrangement on a top end 122 of the scintillator array, and are configured to redirect particles between top ends of crystals of the scintillator array.

Figure 7:
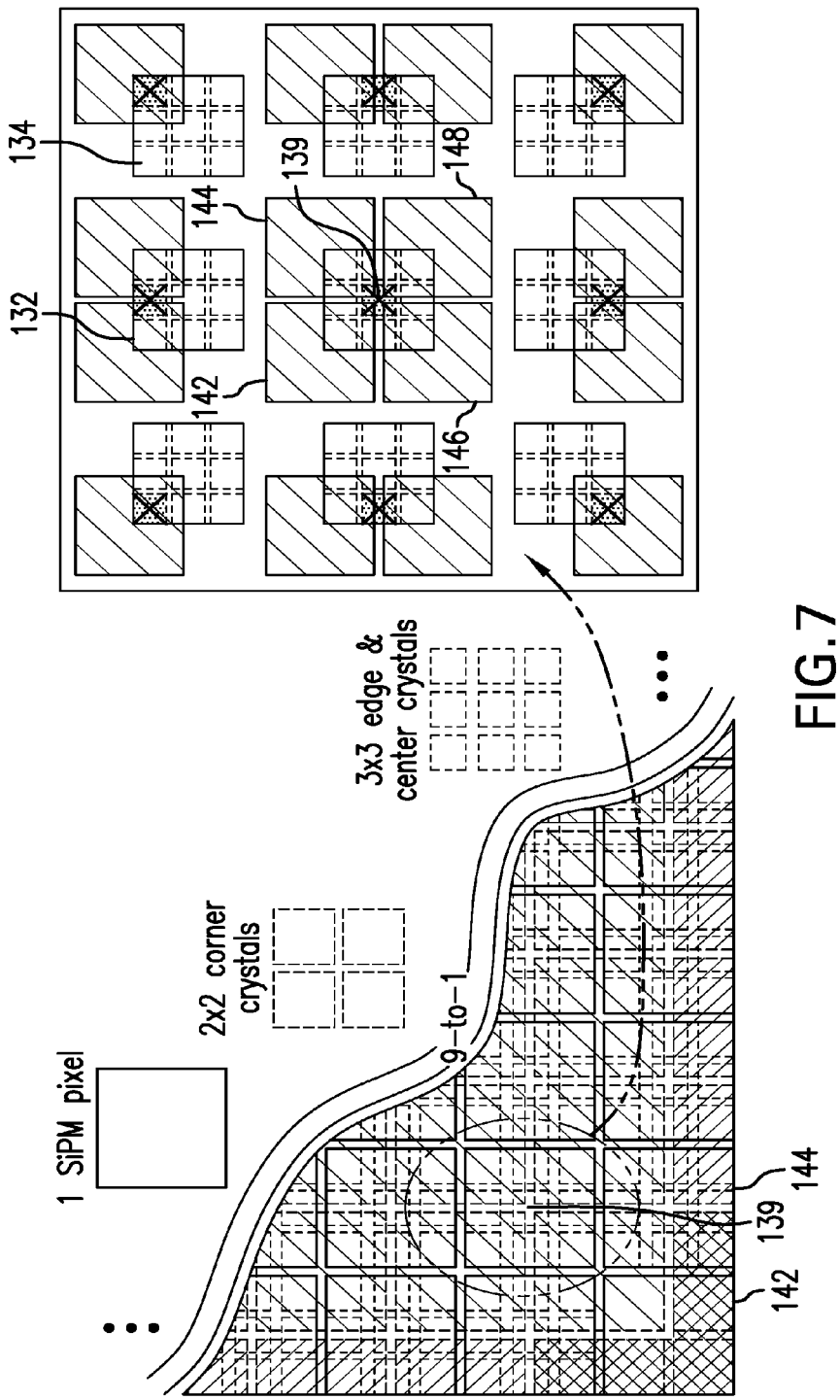
FIG. 7 illustrates arrangements of 9-to-1 coupled Prism-PET module, according to embodiments of the present disclosure, FIG. 8 provides perspective views of a light guide array, according to embodiments of the present disclosure.
Figure 8:
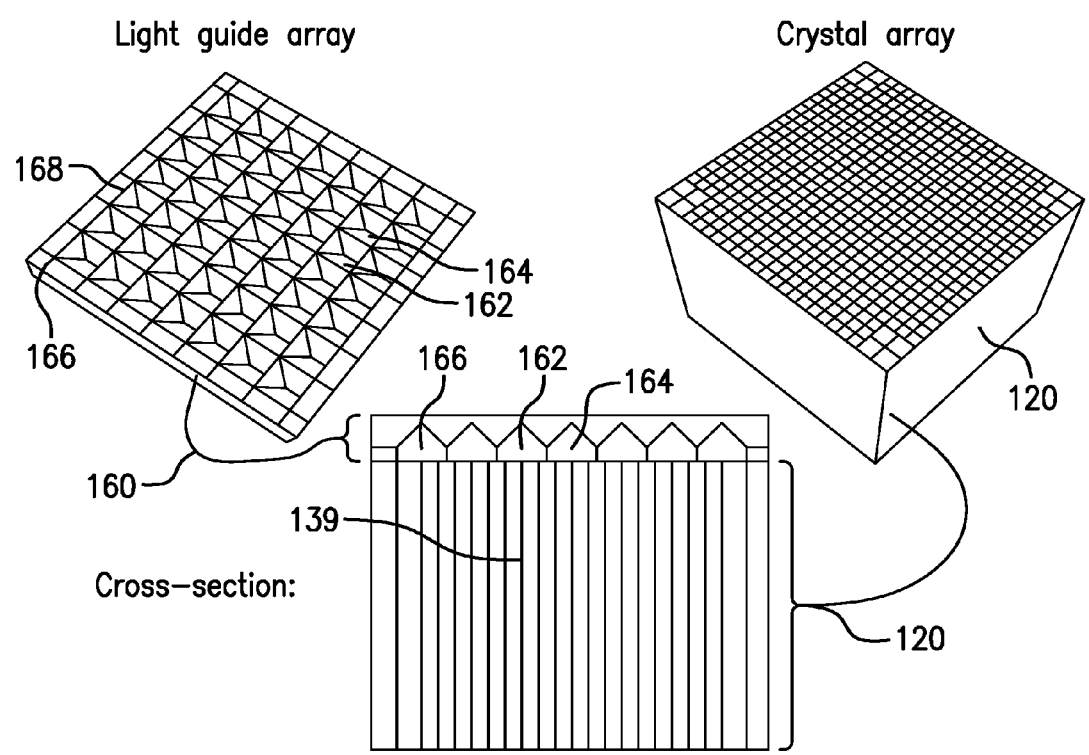

Different Prism-PET detector modules were fabricated for comparison. A first Prism-PET detector 142 consisted of a 16×16 array of 1.4×1.4×20 $mm^3$ lutetium yttrium orthosilicate (LYSO) crystals coupled 4-to-1 on one side to an 8×8 SiPM readout array 140 and on the opposite (radiation-receiving) side to a uniform glass light guide, similar to modules previously studied in the literature [8,20]. A second Prism-PET detector 144 consisted of the same crystal and readout geometry, the conventional single uniform glass light guide was interchanged with a prismatoid light guide array having unique design and layout of prisms at the corner, edge, and center of the detector module to optimize light sharing patterns (FIGS. 5-8). A third Prism-PET detector had the prismatoid light guide array and used the same SiPM array as the other detectors but utilized an ~24×24 array of 0.96×0.96×20 $mm^3$ LYSO crystals to achieve 9-to-1 coupling (FIG. 7 and FIG. 8). In both Prism-PET detector modules, scintillator crystals are coupled to readout pixels and right triangular prisms in equal ratios.

The coupling scheme of the prisms is offset from that of the readout pixels, such that each crystal is only coupled to other crystals belonging to different readout pixels (FIG. 5). When optical photons enter the prismatoids following gamma ray interactions in the crystals, the photons (i.e. particles 300) are efficiently redirected to neighboring crystals due to the right triangular prism geometry, enhancing the light sharing ratio between pixels (FIG. 2). The geometry of each prismatoid is position dependent and predefined to decouple adjacent crystals along edges and corners that would otherwise have similar readout patterns in order to optimize crystal separation. In certain embodiments of the present disclosure, a first group comprises four crystals and a second group comprises four crystals, and the first group and the second group share two adjacent crystals of the four crystals. In certain embodiments, only the shared crystals are configured to direct particles to both the first detector and the second detector.

As illustrated in FIGS. 7 and 8, a first prismatoid 162 of the plurality of prismatoids is configured to redirect particles between top ends 122 of a group of nine crystals of the scintillator array 120. In embodiments of the present disclosure, a center crystal 139 of the group of nine crystals is configured to direct particles to four adjacent detectors 142, 144, 146, 148, a second prismatoid 164 of the plurality of prismatoids is configured to redirect particles between top ends of another group of nine crystals of the scintillator array, and the first prismatoid 162 is substantially adjacent to the second prismatoid 164, and the group of nine crystals 132 is substantially adjacent to the another group of nine crystals 134. In embodiments of the present disclosure, a corner prismatoid of the plurality of prismatoids is configured to redirect particles between top ends of a group of five crystals of the scintillator array. In embodiments of the present disclosure, an edge prismatoid 168 of the plurality of prismatoids is configured to redirect particles between top ends of a group of five crystals of the scintillator array.

Because the coupling scheme confines intercrystal light sharing to be between neighboring SiPMs that enhance crystal identification, one can match the index of refraction n between the scintillator columns, prisms, and coupling adhesive to further enhance light sharing and consequently improve DOI resolution and crystal identification. All prisms were fabricated using SF10 glass with n=1.767 (instead of BK7 with n=1.53, which is the material for the uniform glass light guide) and coupled to the scintillator arrays using NOA170 adhesive with n=1.7. Barium sulfate ($BaSO_4$) is used as the reflector material between the crystals and prisms due to its high spatial performance that does not degrade energy or timing resolutions [21]. SiPM saturation effects, which have been known to positively skew energy resolution and negatively impact DOI resolution, were not accounted for at this time [22].

FIG. 6 provides perspective views providing details of the prismatoid array, according to embodiments of the present disclosure.

Perspective views of the prismatoid array, a cross-section of the prismatoid and respective crystals, and individual view of corner, edge and center prismatoids of a 4-to-1 coupled Prism-PET module are provided in FIG. 6. The bottom ends of a first group of crystals of the scintillator array illustrated in FIG. 6 are configured to direct particles to a first detector of the plurality of detectors, and the bottom ends of a second group of crystals of the scintillator array are configured to direct particles to a second detector substantially adjacent to the first detector.

FIG. 7 illustrates arrangements of 9-to-1 coupled Prism-PET module according to embodiments of the present disclosure. The inset of FIG. 7 illustrates the predefined readout pattern of each crystal belonging to a single prismatoid light guide in the 9-to-1 coupled module.

FIG. 8 provides perspective views of a light guide array, a prismatoid crystal array, and a cross-section of the prismatoid of the 9-to-1 coupled Prism-PET module according to embodiments of the present disclosure.

Advantages are demonstrated using experimental measurements in terms of crystal identification, energy resolution, and DOI resolution, including how Prism-PET enables up to 9-to-1 crystal-to-readout coupling, which can be used to substantially improve spatial resolution without increasing the number of readout channels (FIGS. 7 and 8).

Figure 9:
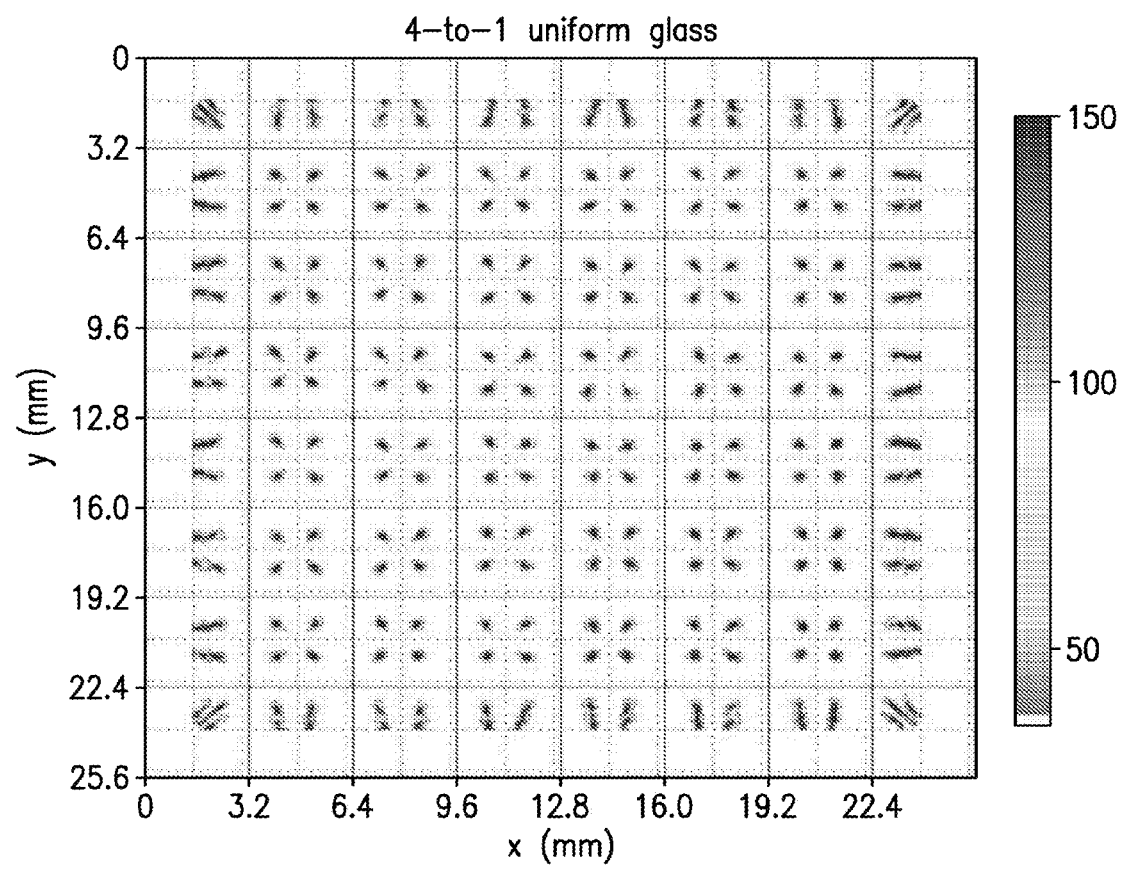
FIG. 9 illustrates a detector readout for 4-to-1 with uniform glass in accordance with known detector module.
Figure 10:
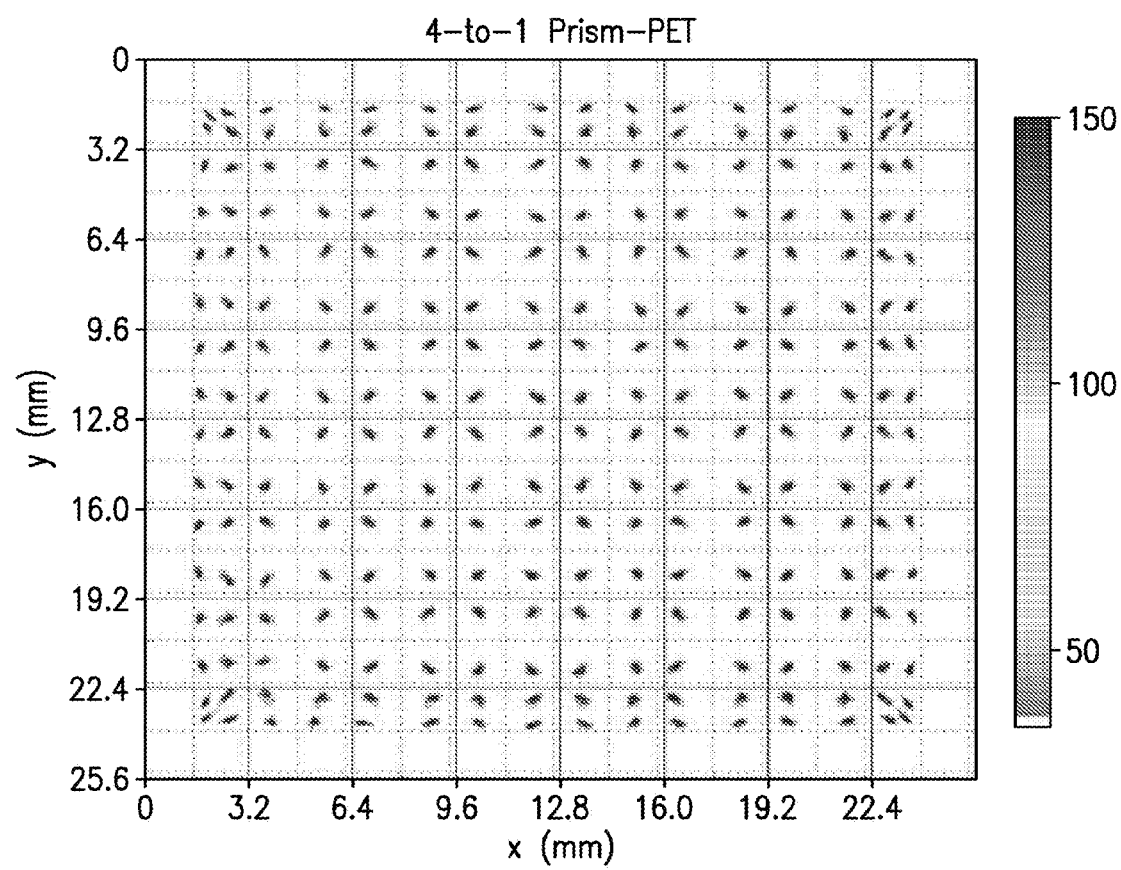
FIG. 10 illustrates a detector readout of 4-to-1 coupled Prism-PET module, according to embodiments of the present disclosure.
Figure 11:
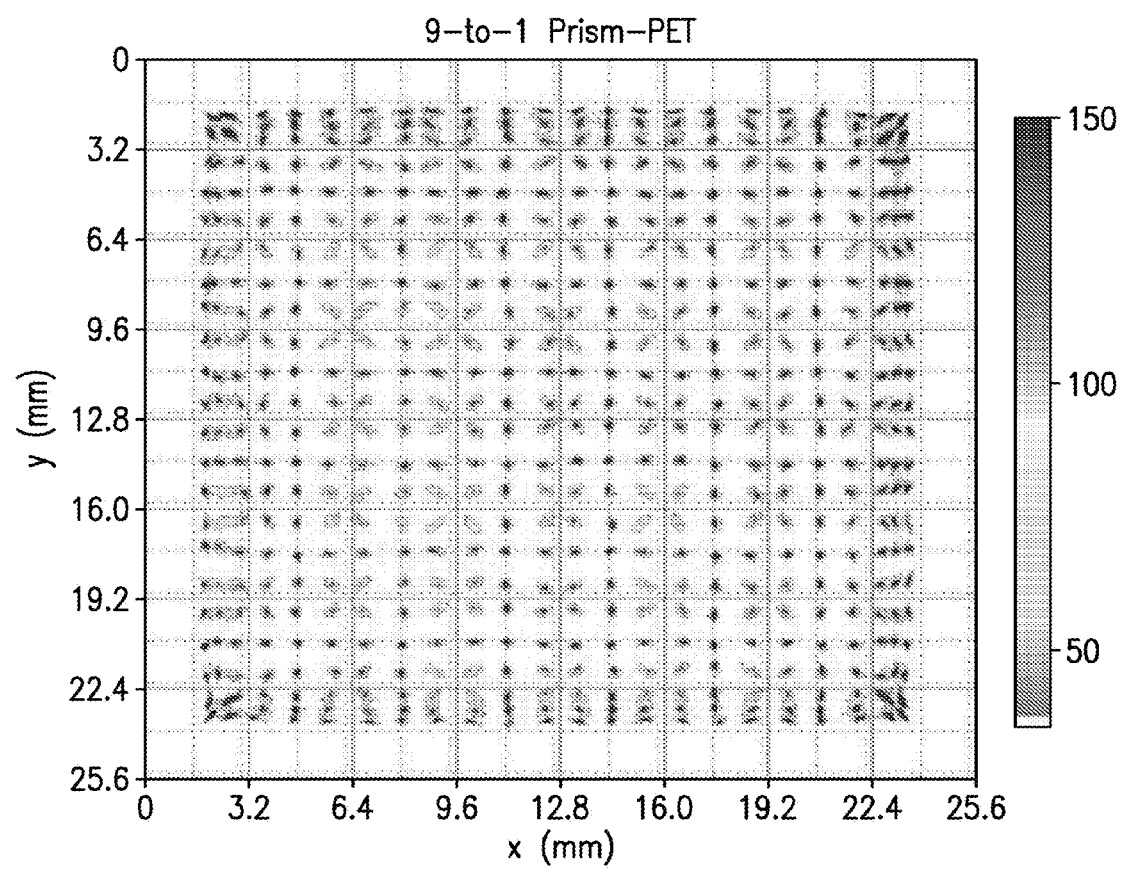
FIG. 11 illustrates a detector readout of 9-to-1 coupled Prism-PET module, according to embodiments of the present disclosure, FIG. 12 provides crystal identification histograms based on centroiding and measured energy histograms with and without DOI filtering, comparing results of a detector readout for 4-to-1 with uniform glass in accordance with known detector module and results using detector modules according to embodiments of the present disclosure, FIG. 13A provides DOI resolution of the uniform glass light guide module of known detector module, FIG. 13B provides DOI resolution of 4-to-1 coupled Prism-PET module according to embodiments of the present disclosure and FIG. 13C provides a comparison of DOI resolution of the two, FIGS. 14A-14D provide measured DOI resolution graphs of the 4-to-1 coupled Prism-PET module, according to embodiments of the present disclosure, FIGS. 15A-15D provide sensitivity graphs and dimensions of several different PET scanners, according to embodiments of the present disclosure.

FIG. 9 illustrates a detector readout for 4-to-1 with uniform glass (known configuration). FIG. 10 illustrates a detector readout of 4-to-1 coupled Prism-PET module, according to embodiments of the present disclosure. FIG. 11 illustrates a detector readout of 9-to-1 coupled Prism-PET module, according to embodiments of the present disclosure.

The detector modules consisted of LYSO crystal arrays fabricated at X-Lum (Shanghai, China) coupled (either 4-to-1 and 9-to-1) to 8×8 arrays of SiPMs (Hamamatsu 513361-3050AE-08). Data acquisition was performed using TOFPET2 application-specific integrated circuits (ASICs) and a FEB/D v2 readout board from PETsys Electronics. Flood data was acquired on 4-to-1 and 9-to-1 coupled detector modules with prismatoid light guide arrays by uniformly exposing the modules with a 3 MBq Na-22 sodium point source (5 mm active diameter). 10,000,000 events from the 4-to-1 module and 22,500,000 events from the 9-to-1 module (to acquire an equal number of events per crystal) were used for flood histogram generation.

Figure 12:
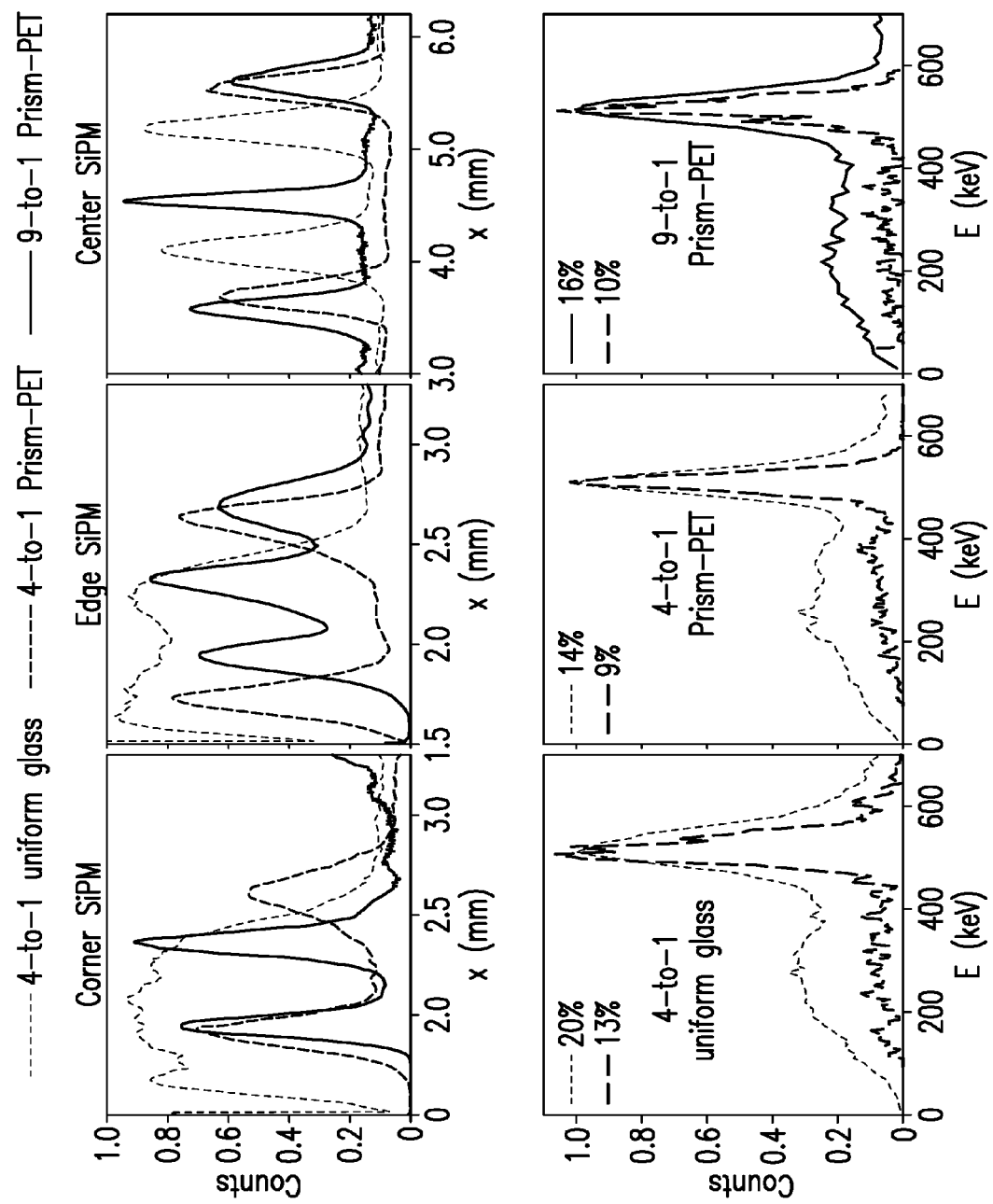

FIG. 12 provides Gaussian histograms and filtered energy spectrums for the 4-to-1 uniform glass of FIG. 9 (known configuration), the 4-to-1 Prism-PET module of FIG. 10, and the 9-to-1 coupled Prism-PET module of FIG. 11. The upper half of FIG. 12 are 1D Gaussian histograms showing crystal separation in the x-direction from a corner, edge and center readout pixel for the modules of FIGS. 9-11. The bottom half of FIG. 12 are filtered energy spectrums with (13%, 9% and 10%) and without (20%, 14%, 16%) DOI-correction from a center crystal in FIGS. 9-11.

DOI performance was experimentally measured on a per-crystal basis using a similar approach described in Ref. [18]. The modules were exposed to a Na-22 source at five different crystal depths (2, 6, 10, 14 and 18 mm) using lead collimation. The source was placed in a lead cylinder with a 1 mm pinhole. The pinhole was aligned with the DOI-aligned module on one side and a single 1.4×1.4×20 mm$^3$ crystal on a reference module on the other side. Coincidence events between the two modules were used to reject scatter events and only accept events along the intended line of response. The histograms for the DOI-estimation parameter [18], w, were calculated and plotted for all crystals. The w histograms were then converted to DOI space using linear regression to determine the slope between w and the ground truth DOI, which should be the center of each Gaussian peak. The widths of the Gaussian peaks converted to DOI space were used to calculate the DOI resolution of the crystals (FIG. 14A-14D). DOI resolution is depth-dependent and equal to the FWHM of the Gaussian histograms. Overall crystal-specific DOI resolution was calculated as the average of the DOI resolutions across the measured depths [18]. A typical center crystal from each module was used to calculate the DOI resolutions of each module.

The spatial performance of Prism-PET modules of the present disclosure is characterized compared with standard uniform glass light guide module using flood histograms of fabricated modules (FIGS. 9-11). The glass light guide module suffers from edge and corner effects, resulting in poor position-dependent crystal separation. Prism-PET enables excellent crystal separation throughout the entire detector array without edge and corner artifacts, which has not previously been achieved in a 4-to-1 coupled detector module with single-ended TOF-DOI readout [8,19,20]. Similar results are shown with the 9-to-1 coupled Prism-PET module (FIG. 11), demonstrating homogenous sub-millimeter crystal separation in a TOF-DOI PET detector module with 3.2×3.2 mm$^2$ SiPM pixels. Plotting 1D event positioning histograms (in the x-direction) confirms that Prism-PET of the present disclosure has uniform crystal separation performance at the center, edges and corners. Prism-PET also achieves 14% and 16% energy resolution with DOI correction in the 4-to-1 and 9-to-1 coupled modules, respectively, whereas the uniform light guide only achieves 20% energy resolution (FIG. 12, bottom graphs).

For the modules of FIGS. 10 and 11. The histograms of FIGS. 13A-13C provide DOI resolution calculated at interaction depths.

Figures 13A, 13B, 13C:
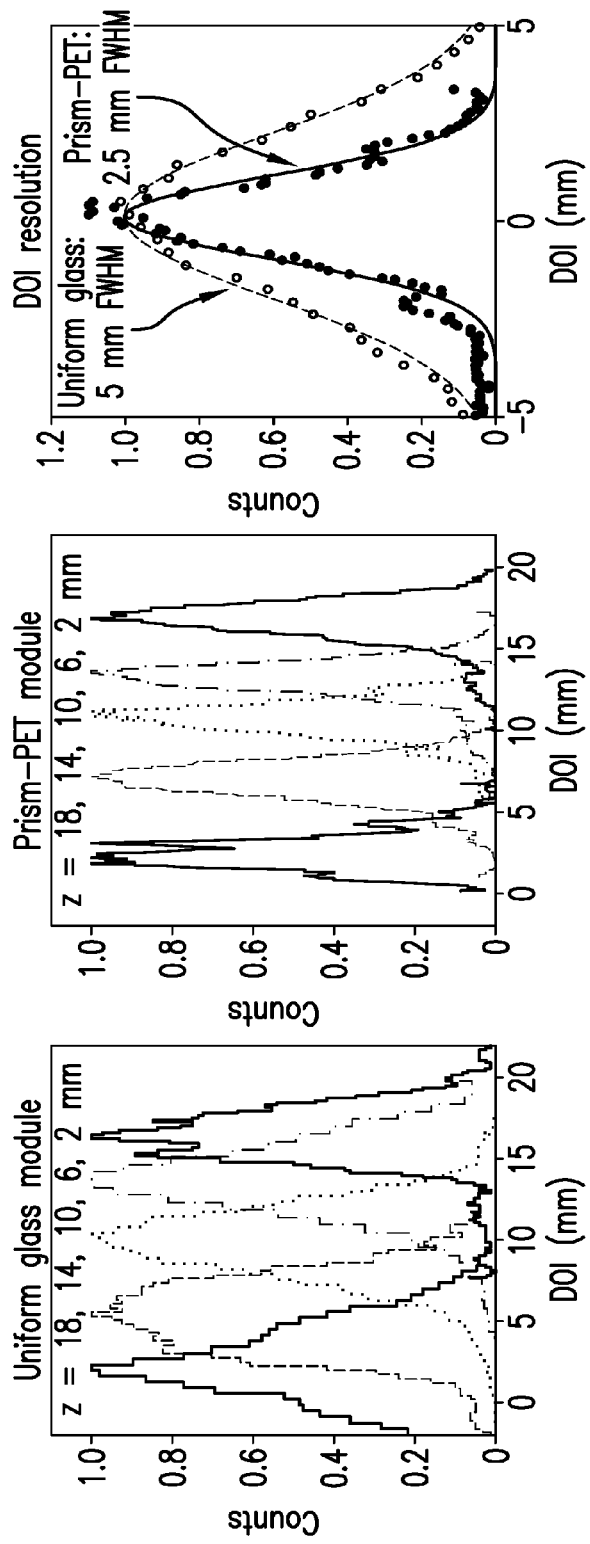

FIG. 13A provides DOI resolution in a center crystal of 4-to-1 coupled detector modules with uniform glass (known configuration).

FIG. 13B provides DOI resolution with prismatoid light guides.

FIG. 13C provides a comparison of DOI resolution based on the light guide used, showing that the Prism-PET detector module of the present disclosure achieves a two-fold improvement in DOI resolution over the uniform glass light guide, as experimentally measured for a single center crystal in each module. The measured DOI resolution for the glass light guide was 5 mm FWHM, showing strong agreement with previously reported results [19]. The Prism-PET modules achieved 2.5 mm FWHM DOI localization, the best resolution ever reported using single-ended readout. Increased depth-dependence of the w parameter is due to 1) controlled and deterministic light sharing pattern within the prismatoids, 2) increased light transfer from scintillators to light guides due to matched refractive indices, and 3) enhanced deviation of upward traveling optical photon path by 180° due to the right triangular prism geometry, all of which enhance light sharing between crystals coupled to the same prismatoid. DOI information can be used to improve both timing and energy resolution, the former by deconvolving depth-specific photon transport inside the scintillator and the latter by constructing depth-specific photopeaks [8,18]. Embodiments of the present disclosure achieved 9% and 10% energy resolution in the 4-to-1 and 9-to-1 coupled Prism-PET modules, respectively, and 13% energy resolution with the uniform light guide after applying DOI-based correction. Note that the DOI and energy resolution values will slightly change for better and worse, respectively, after implementing SiPM saturation correction [22]; as a result, the reported values are more indicative of the relative performance of Prism-PET of the present disclosure compared with the uniform light guide module rather than the absolute performance in practice.

Figure 14A:
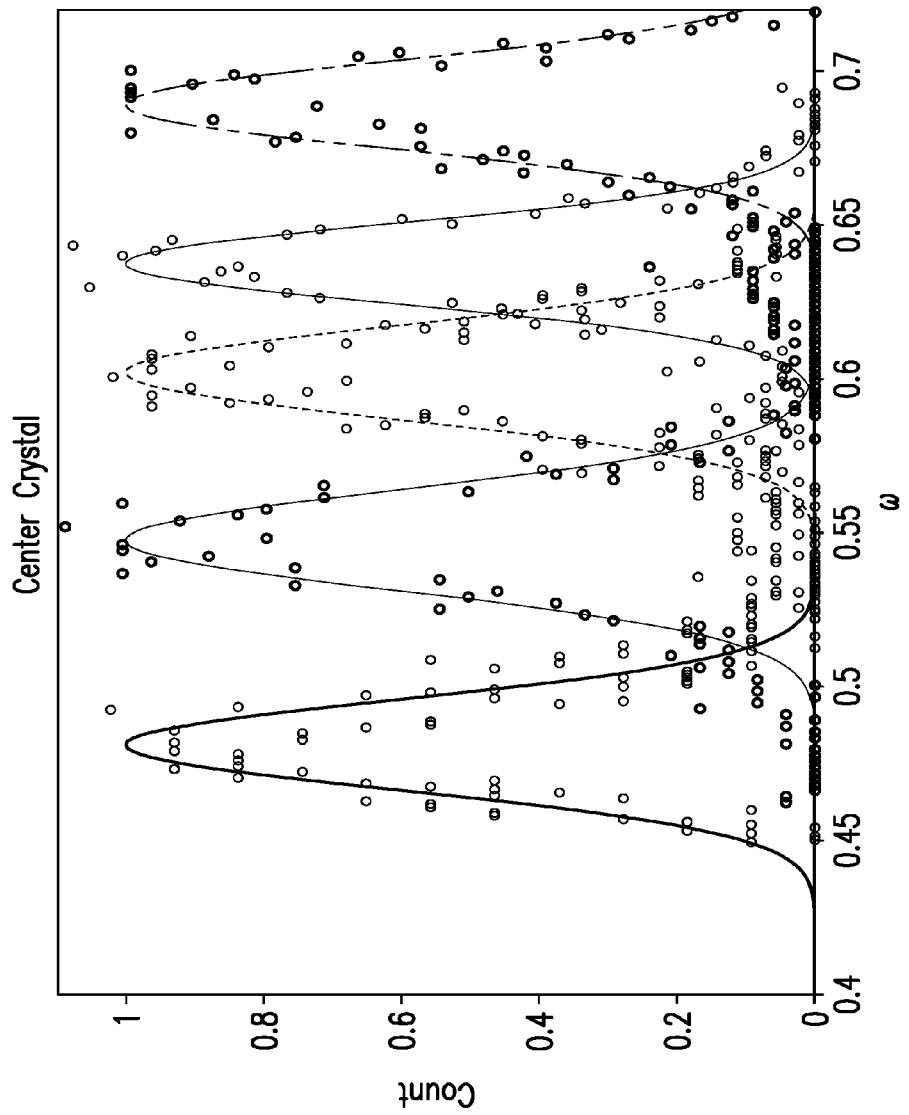
Figure 14B:
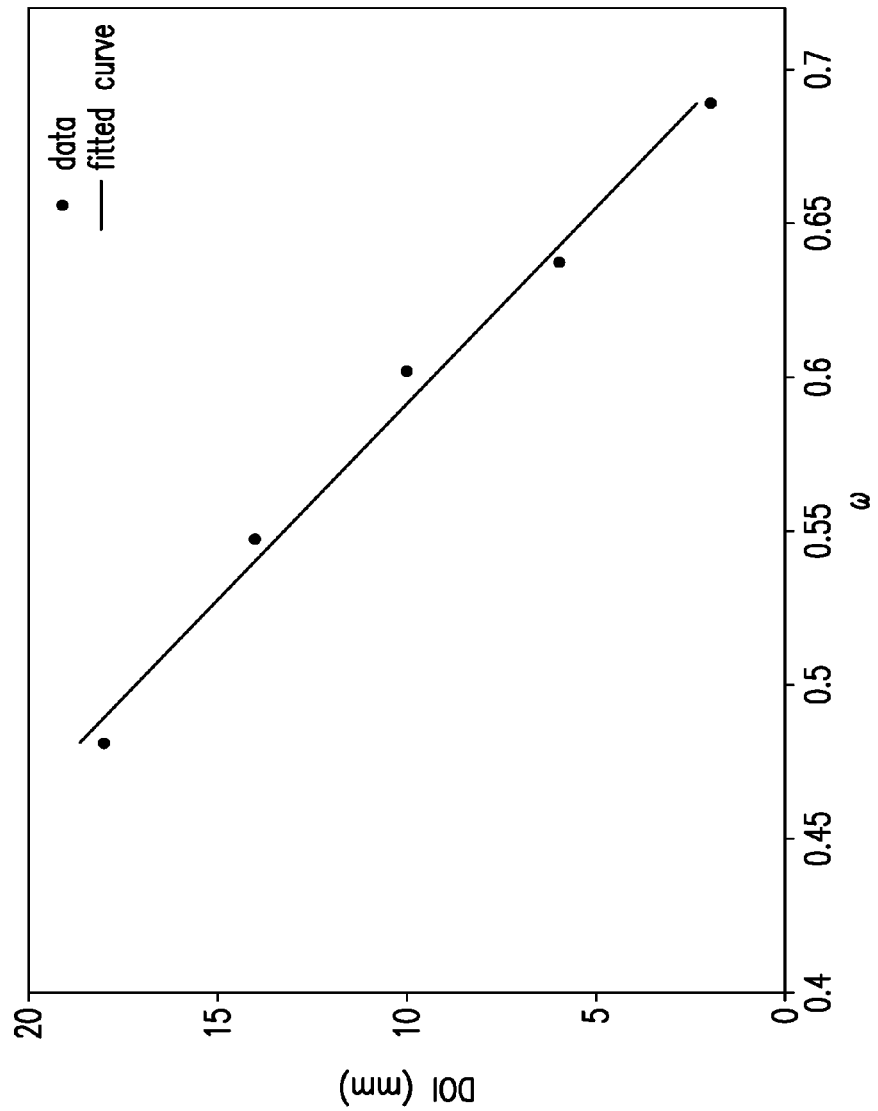
Figure 14C:
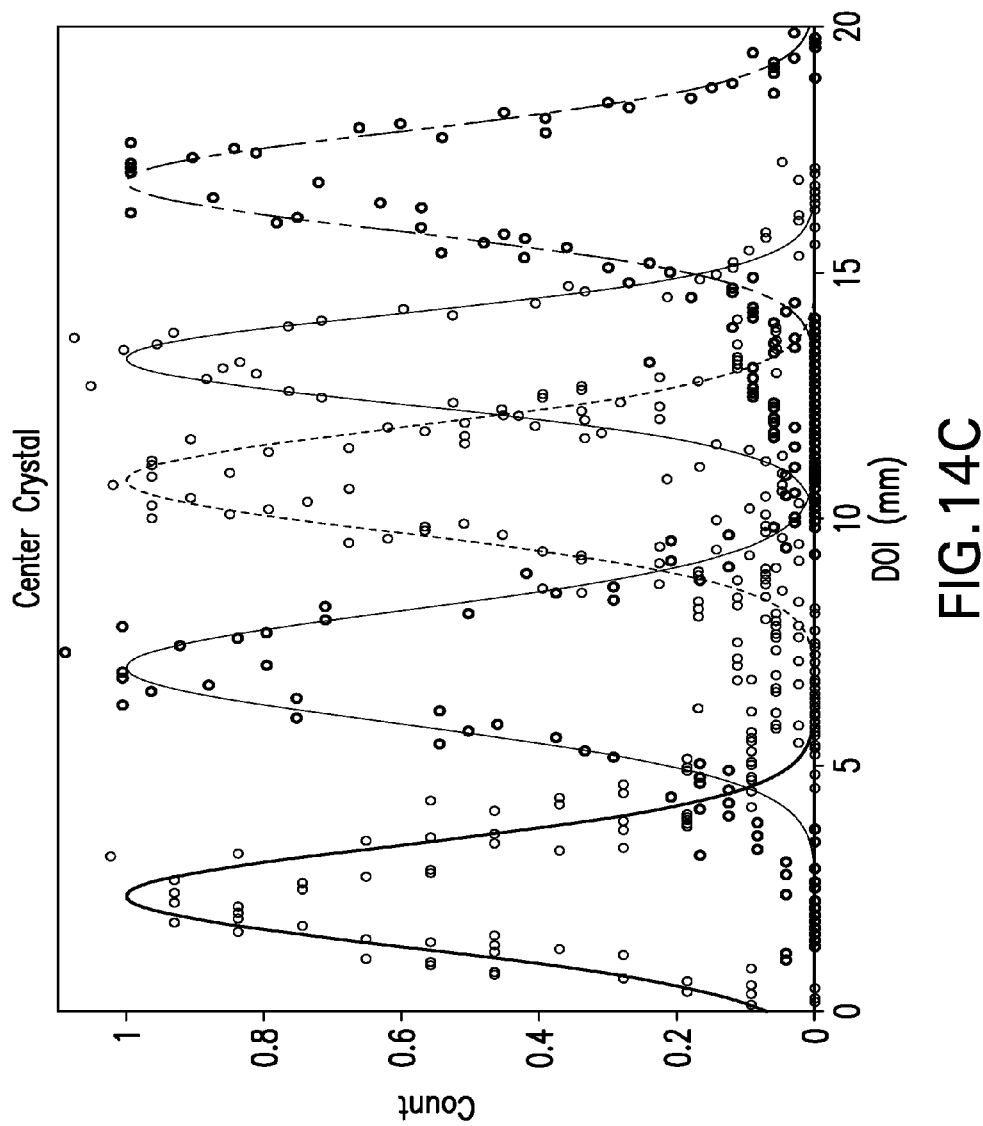
Figure 14D:
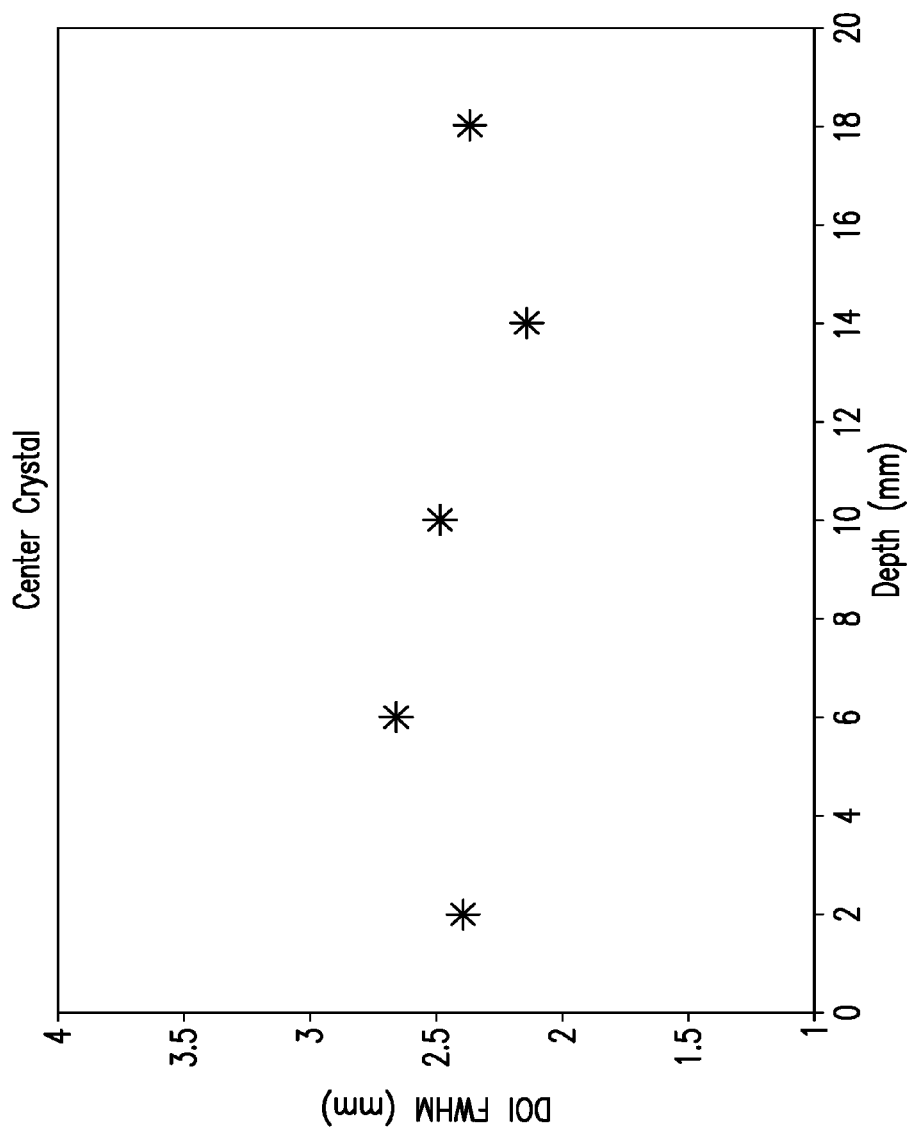

FIGS. 14A-14D provide DOI resolution graphs, according to embodiments of the present disclosure, with conversion from DOI-specific w histograms to DOI histograms showing the DOI resolution of a single crystal at each depth. FIG. 14A provides histograms of the DOI-estimation parameter w acquired at 2, 6, 10, 14 and 18 mm. FIG. 14B provides fit between w and DOI via linear regression. FIG. 14C provides DOI histograms generated by taking the w histograms in FIG. 14A and multiplying by the slope of the linear fit in FIG. 14B. FIG. 14D provides DOI resolution at each acquired depth based on the width of the Gaussians in FIG. 14C.

Perhaps the most important parameter to consider when building a PET system is gamma ray detection sensitivity, which is directly related to signal-to-noise ratio (SNR) and thus determines patient throughput, delivered dose and image quality. Monte Carlo simulations using highly advanced software such as GATE are the most reliable way to model and calculate system-level sensitivity. However, relative improvements in sensitivity and comparisons between systems can be done analytically by calculating (a) geometric sensitivity and (b) sensitivity gain based on coincidence time resolution (CTR) for time-of-flight readout (TOF), which is equal to the SNR gain squared [24] in Equation (1):

$$\Delta(SNR) = \sqrt{\frac{D}{\Delta x}} \qquad (1)$$

$$\Delta(Sens) = \Delta(SNR)^2 = \frac{D}{\Delta x},$$

where D is the diameter of the object being imaged and $\Delta x$ is the length of the reconstructed line segment along the line-of-response, which is directly proportional to the CTR ($\Delta t$) in Equation (2):

$$\Delta x = \frac{c * \Delta t}{2} \quad (2)$$

An example of a dedicated brain PET scanner that can be built with Prism-PET detector modules would be a cylindrical ring with 50 cm axial length and 25 cm diameter.

Figure 15A:
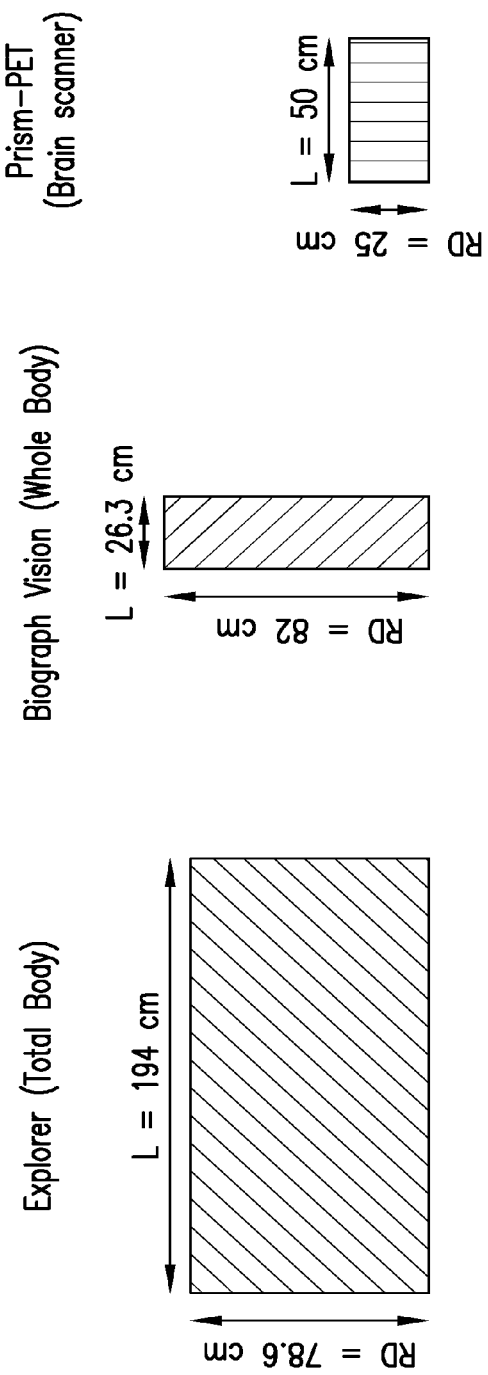
Figure 15B:
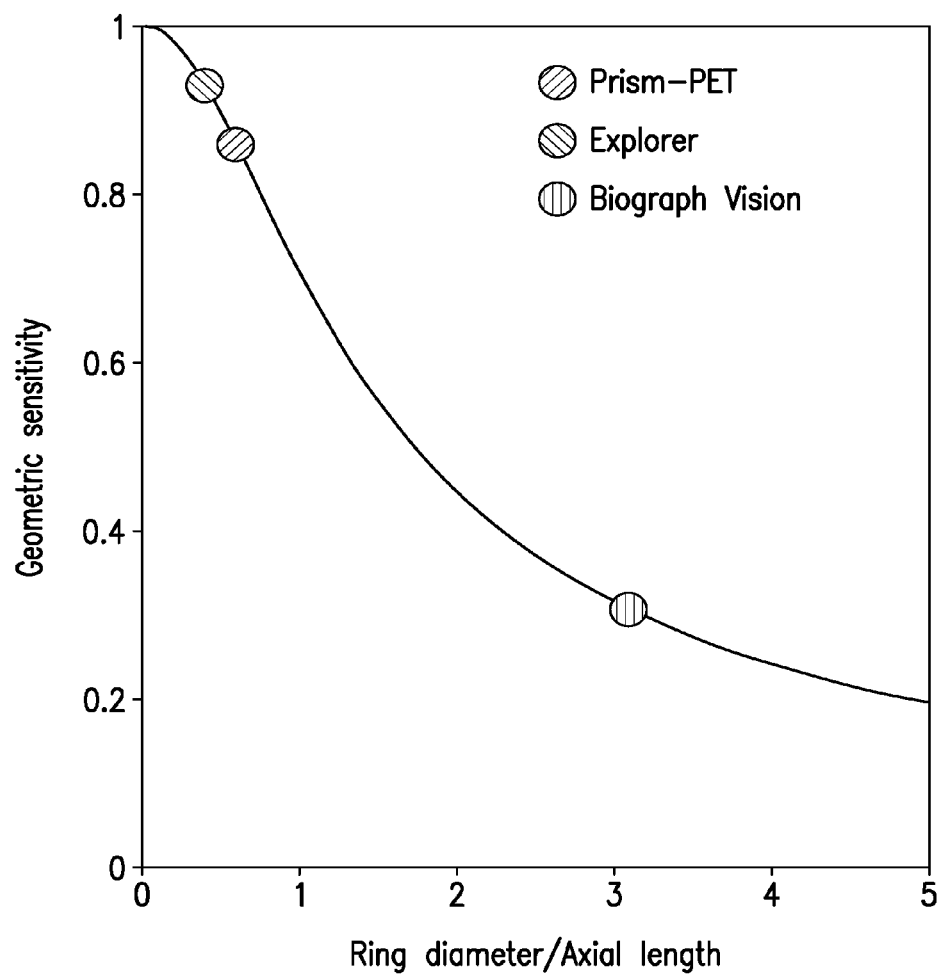
Figure 15C:
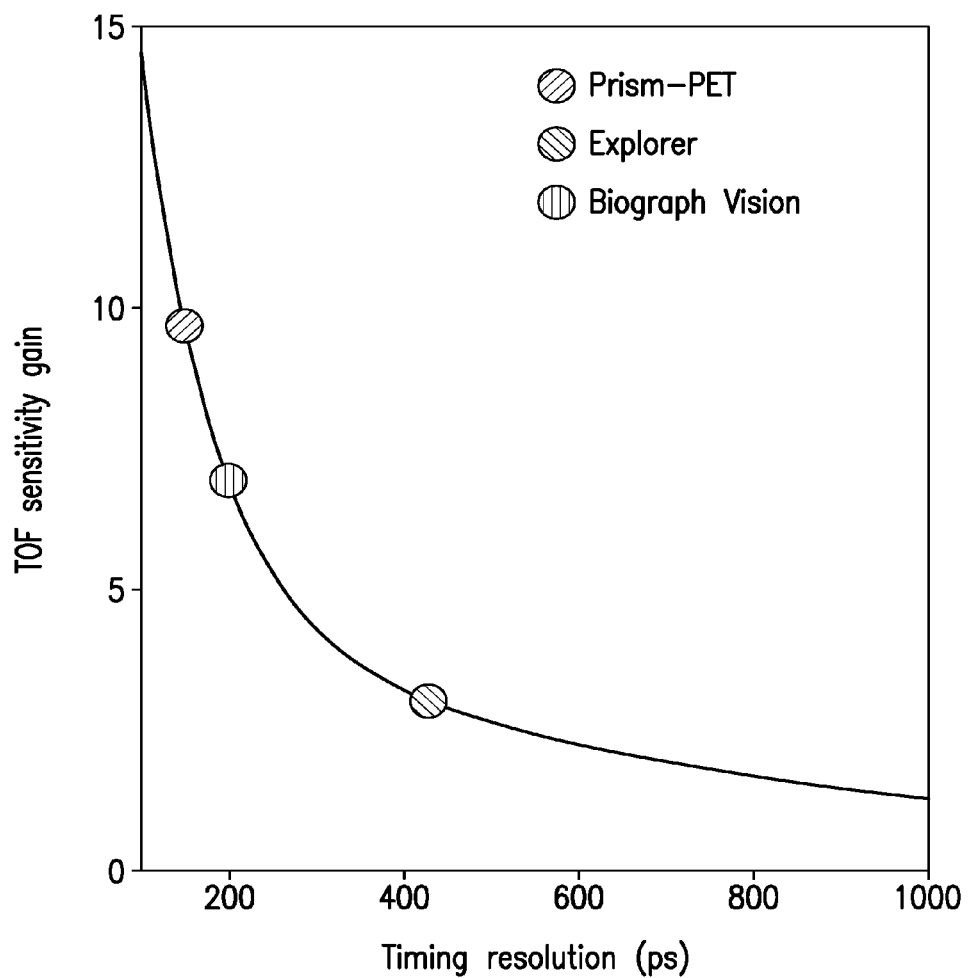
Figure 15D:
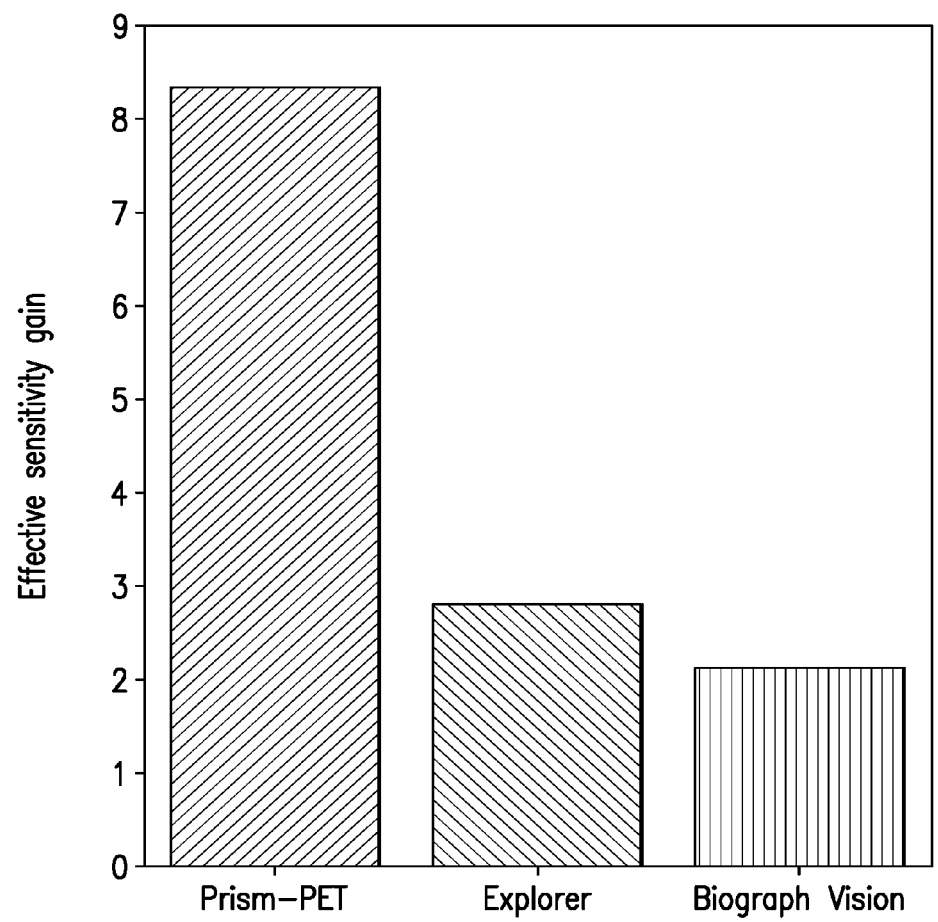

FIGS. 15A-15D provide sensitivity graphs, according to embodiments of the present disclosure. FIG. 15A provides dimensions and geometric coverage of a Siemens Biograph Vision, Explorer Total-Body PET scanner, and an example of a Prism-PET brain scanner. FIG. 15B provides geometric sensitivity for a point source positioned in the center of each of the scanners shown in FIG. 15A. FIG. 15C provides relative sensitivity gain as a function of coincidence timing resolution. FIG. 15D provides effective sensitivity gain calculated as the product between geometric efficiency (as shown in FIG. 15B) and TOF sensitivity gain (as shown in FIG. 15C).

FIG. 15A shows brain Prism-PET scanner dimensions according to embodiments of the present disclosure compared to those of an example whole-body (Siemens Biograph Visions) and total-body (Explorer) PET scanner. Having a small ring diameter and large axial field-of-view greatly improves the geometric efficiency (FIG. 15B) at the cost of greatly increased parallax error and partial volume effect, which can be mitigated by performing depth-of-interaction (DOI) readout [26]. As a result, small diameter organ-specific scanners should only be built with detector modules with DOI localization capabilities, such as our Prism-PET modules.

DOI readout can also be used to recover CTR for TOF readout by deconvolving the DOI-dependence on coincidence timing (i.e., differences in path length in optical photons) [8]. Assuming the same CTR reported as set forth herein (~150 ps), which is a safe lower bound estimate since our modules have better DOI resolution (2.5 mm vs. 3 mm), Prism-PET enables a TOF sensitivity gain close to a factor of 10 based on Eq. (1) when imaging an object with D ~20 cm such as the human brain (FIG. 15C). The TOF sensitivity gain for human brain imaging is slightly lower for Siemens Biograph Vision, which achieves ~220 ps CTR [25], and much lower for the Explorer (FIG. 15C), which has CTR>400 ps [23].

FIG. 15D shows the overall effective sensitivity gain for human brain imaging when taking both geometric efficiency and TOF sensitivity gain into account. Based the above calculations, the Prism-PET scanner in embodiments of the present disclosure enables a three-fold and four-fold improvement in sensitivity compared to the Siemens Biograph Vision and Explorer scanners, respectively.

FIGS. 16A-16F illustrate Compton interaction, according to embodiments of the present disclosure.

Regarding Compton interaction, Prism-PET of the present disclosure enables Compton scatter energy decomposition (and thus localization) due to its deterministic light sharing pattern. Let's assume we have a 16×16 array of lutetium LYSO crystals with a Prism-PET light guide coupled 4-to-1 to an 8×8 array of silicon photomultiplier (SiPM) pixels. Based on an approximation that each 511 keV gamma rays will produce a signal on 4 different pixels due to light sharing, the light sharing ratios between all crystals belonging to the same prismatoid can be measured directly using photoelectric events from flood data. Using this information, the energies of the primary interaction (i.e., recoil electron) and secondary interaction site (i.e., scattered gamma ray) are decomposed. Once the decomposed energies are obtained, the two independently absorbed events in the scintillation blocks can be localized and the scattering angles and DOI can be determined. For the Prism-PET module of the present disclosure, identifying a side-by-side Compton scattering event is possible because of the change from random light sharing for photoelectric events to a deterministic pattern (FIGS. 16 and 17).

Figure 16A:
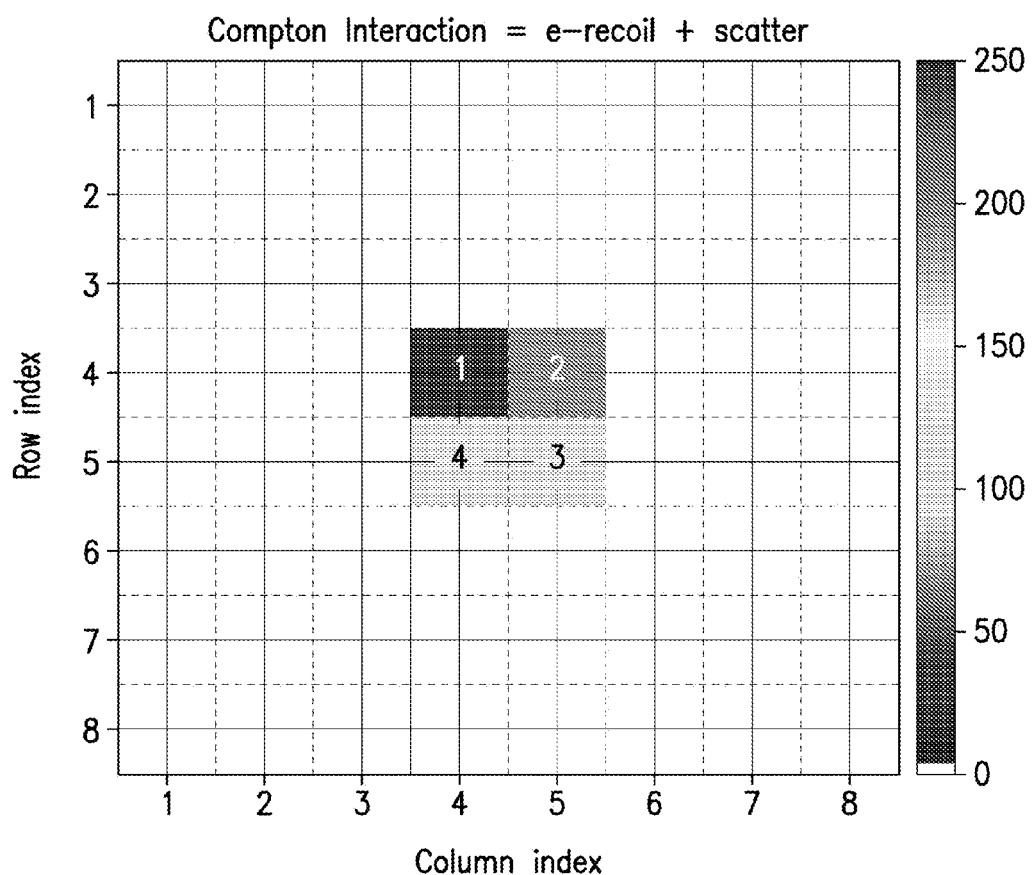
FIGS. 16A-16F illustrate theoretical light distribution for a side-by-side Compton interaction in the 4-to-1 coupled Prism-PET module, according to embodiments of the present disclosure.
Figure 16B:
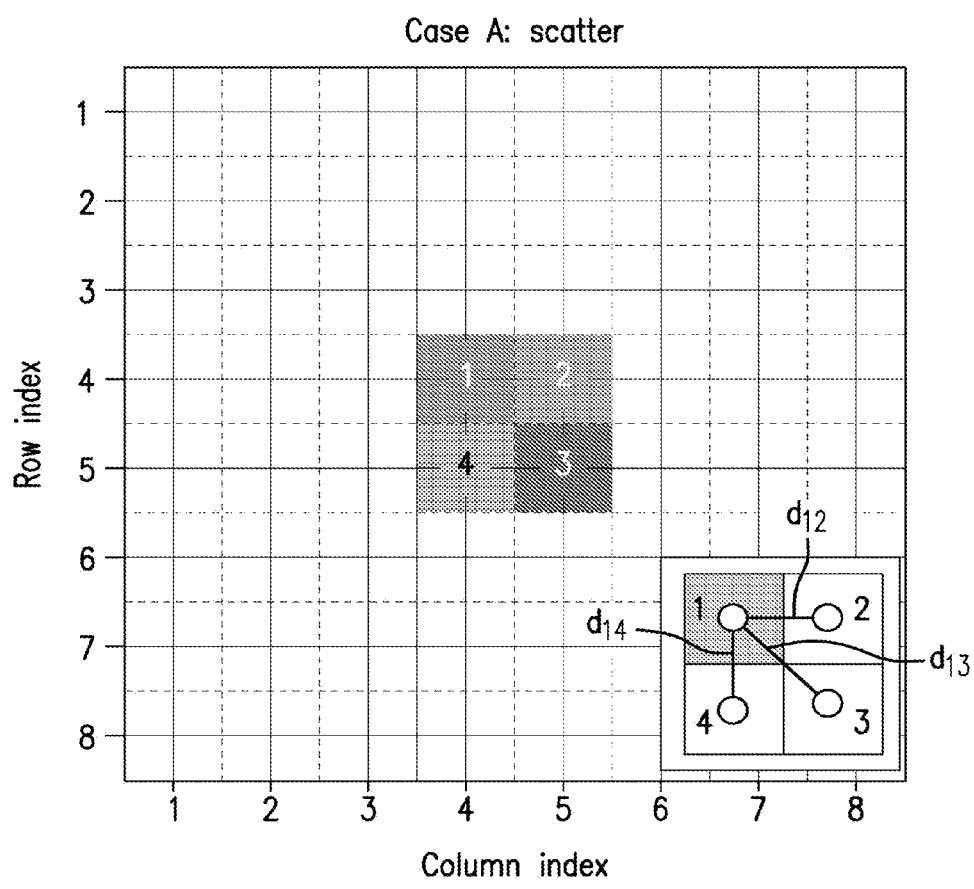
Figure 16C:
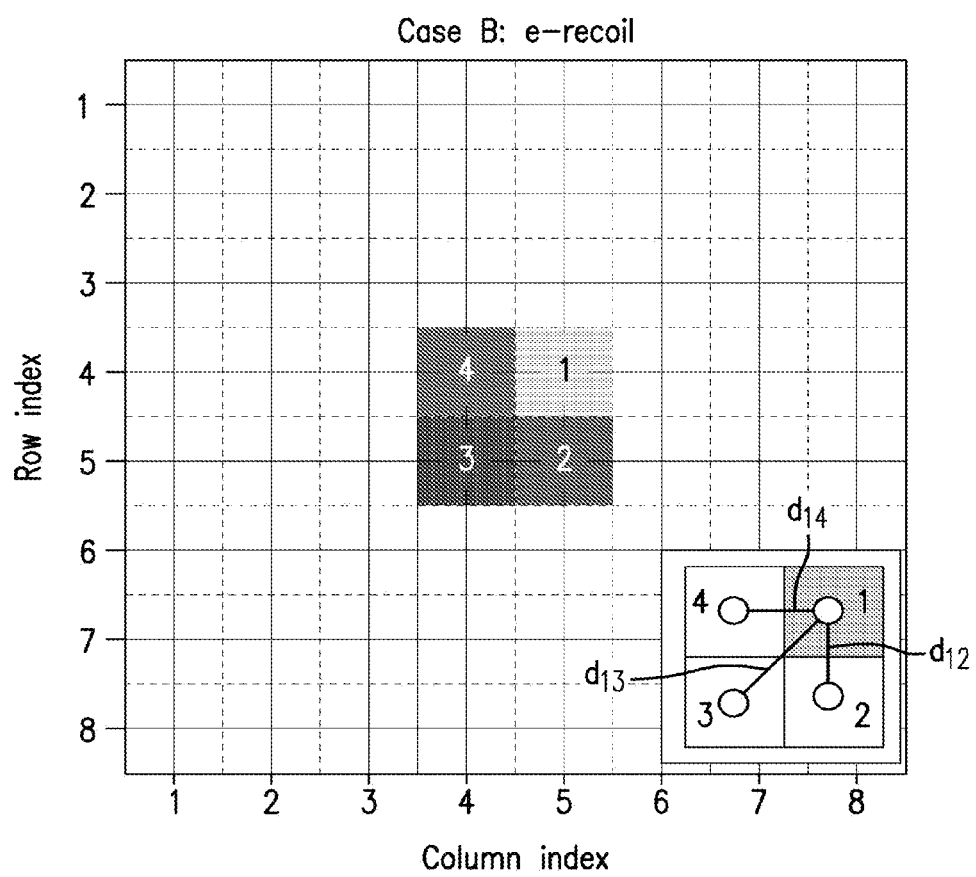
Figure 16D:
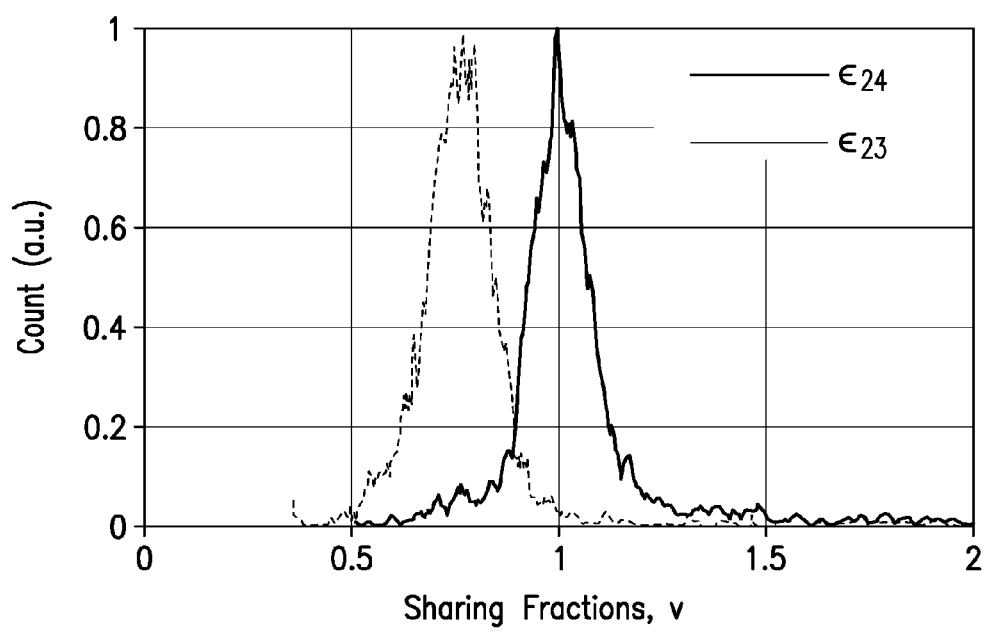
Figure 17:
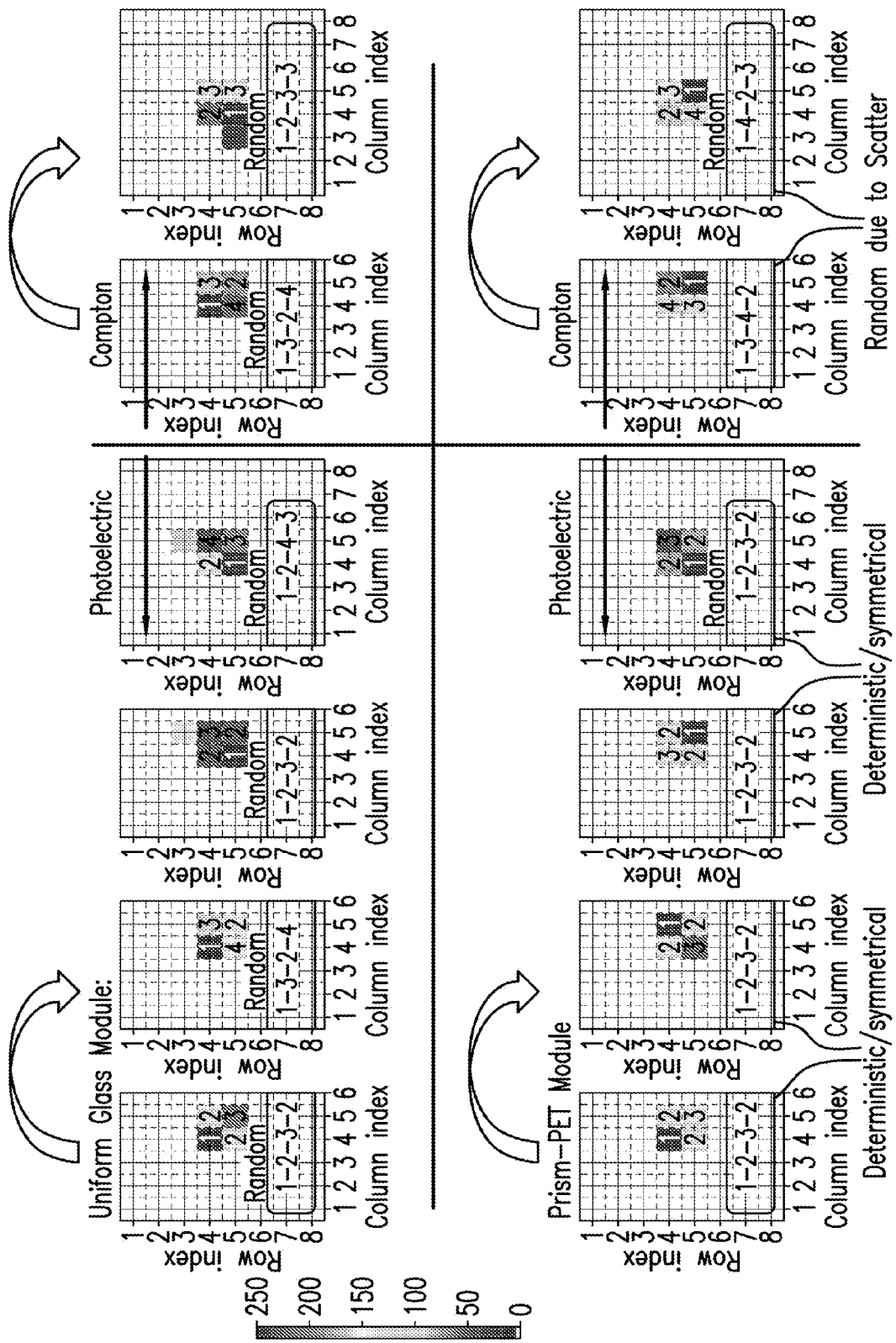
FIG. 17 illustrates photoelectric and Compton interaction measurements in the 4-to-1 coupled Prism-PET module, according to embodiments of the present disclosure.

FIGS. 16A-16C provide example of Compton energy decomposition in a multicrystal scintillator array with Prism-PET of the present disclosure. FIG. 16D provides examples of light sharing fraction ratios between pixel 1 and neighboring pixels, as labeled in FIGS. 16A-16C. In one case, both pixels (2 and 4) are adjacent to pixel 1 resulting in equal light sharing fractions, while in the other case pixel 3 is diagonally across from pixel 1 resulting in a smaller light sharing fraction. (E), (F) Energy and DOI error of Compton interaction decomposition for Prism-PET.

Classical Compton energy decomposition can be performed as follows. The total absorbed energies EA and EB by the constituent elements A and B (scatter and recoil electron) are given as the summation of the energies in all 4 SiPMs in Equation (3):

$$E_A = \sum_{i=1}^{4} E_{Ai}$$

$$E_B = \sum_{i=1}^{4} E_{Bi}, \quad (3)$$

where $E_{A1}$ and $E_{B1}$ are the maximum deposited energies in the SiPM coupled to the interacted crystal pixels and $E_{A2,3,4}$ and $E_{B2,3,4}$ are the deposited energies in the neighboring columns due to light leak at the bottom (from the SiPM side) and at the top via the prism-mirror light guide. The experimental results in FIG. 16A illustrate the four known parameters $E_{1-4}$ corresponding to the detected energies by each of the four pixels after the side-by-side Compton scattering event, where the total gamma particle energy deposited is provided by Equation (4):

$$E_\gamma = E_A + E_B \quad (4)$$

Note that the energies of the constituent elements of the Compton scattering event, namely $E_{A1-4}$ and $E_{B1-4}$, are unknown. Writing the equations based on the measured energies obtains Equation (5):

$$E1 = EA1 + EB4$$

$$E2 = EA2 + EB1$$

$$E3 = EA3 + EB2$$

$$E4 = EA4 + EB3, \quad (5)$$

providing 4 equations and 8 unknowns. However, the deposited energies in the neighboring columns are correlated. Considering the inset plot in FIG. 16D where the maximum deposited energy occurred in the top-left SiPM. Given that the sharing fraction with the three neighbors depends on their proximity to the interacted crystal, and using the Pythagorean theorem by forming a right triangle using centers of the three neighbors as its vertices, we arrive at Equation (6):

$$\in_{24}=d_{12}/d_{14}=1 \xrightarrow{thus} E_{A4}=\in_{24}E_{A2}=E_{A2}$$

$$\in_{23}=d_{12}/d_{13}=1/\sqrt{2}=0.7 \xrightarrow{thus} E_{A3}=\in_{23}E_{A2}=0.7E_{A2}, \quad (6)$$

where, for example, $d_{12}$ is the distance between the centers of the primary SiPM 1 and neighboring SiPM 2. Substituting Eq. 6 in Eq. 5 we get Equation (7):

$$E1=E_{A1}+E_{B2}$$

$$E2=E_{A2}+E_{B1}$$

$$E3=0.7E_{A3}+E_{B2}$$

$$E_4=E_{A4}+0.7E_{B2}, \quad (7)$$

where we now have 4 equations and 4 unknowns. Note that in practice the sharing fractions will have spatial variations from the ideal cases shown in Eq. 6 due to some small and unavoidable misalignments between the prism-mirror light guides and the scintillator columns. However, as shown in FIG. 16D, they can be obtained empirically across the array by analyzing the sharing fractions from individual photoelectric events obtained using the flood-histogram experiment.

FIGS. 16B and 16C depict the two decomposed elements of a measured side-by-side Compton scattering event based on the above analysis.

Given that our modules have DOI localization, we can represent the DOI variables as Equation (8):

$$w_A=E_{A1}/E_A$$

$$w_B=E_{B1}/E_B \quad (8)$$

Figure 16E:
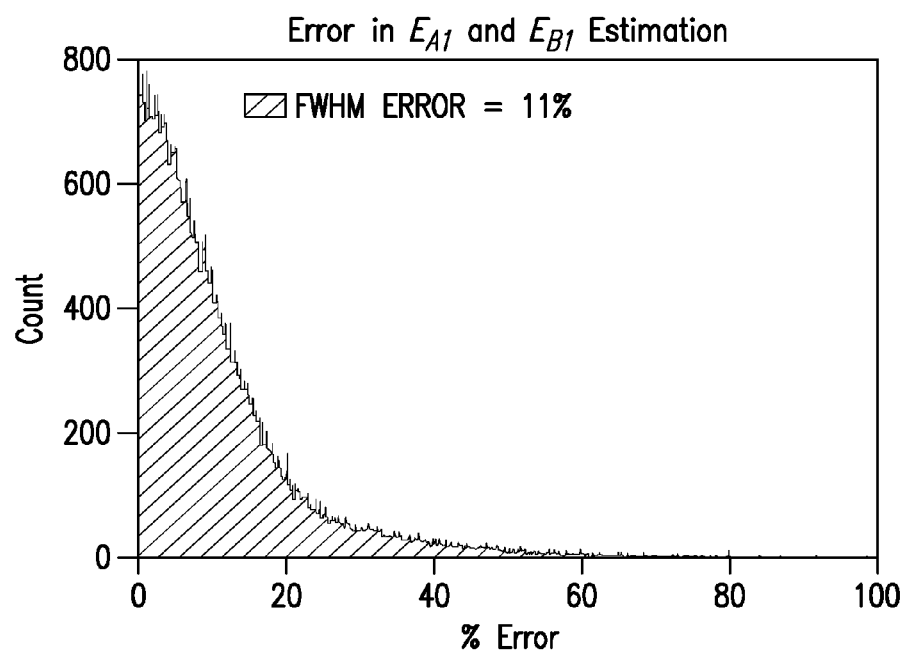
Figure 16F:
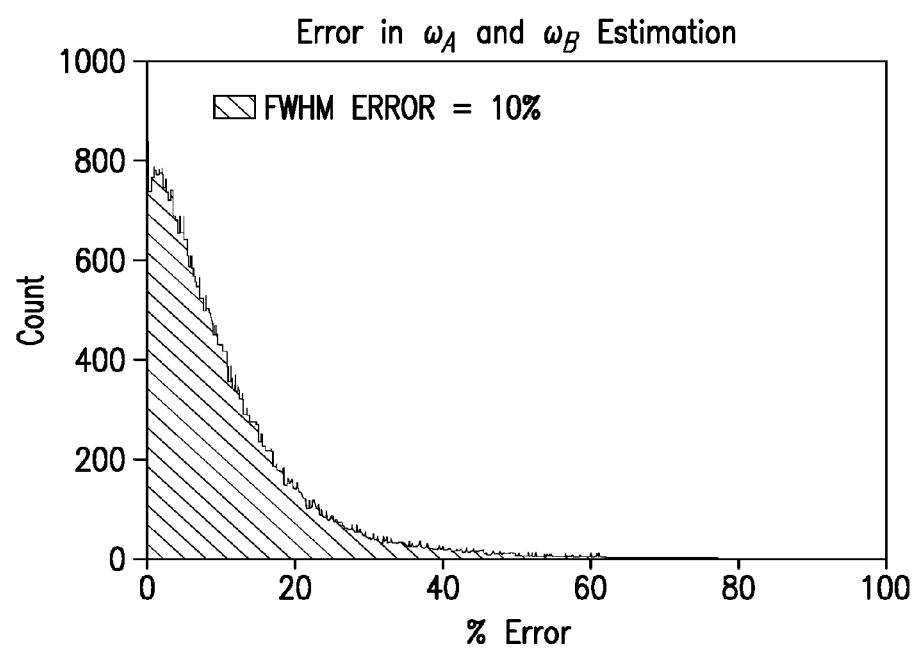

As shown in FIGS. 16E and 16F, the percent error for our estimation of $\{E_{A1},E_{B1}\}$ and $\{w_A,w_B\}$ based on 200,000 experimental Gamma events is ~10%. The error can be further reduced using convolutional neural networks as the estimator specially since we can collect millions of Gamma events as training dataset using the flood-histogram experiment.

An example of how a Compton event where the recoil electron and scattered γ-ray are fully absorbed in adjacent scintillators in two different SiPMs can be decomposed into its constituent elements can be seen in FIGS. 16A-16D. Calculating the DOI variable w using classical Compton decomposition resulted in 11% full width at half maximum (FWHM) error (FIG. 16E). In addition, Compton decomposition results in 15% FWHM energy error (FIG. 16F).

FIG. 17 illustrates photoelectric and Compton interaction, according to embodiments of the present disclosure, in which graphs of random light sharing pattern of a glass light guide are provided above graphs of deterministic light sharing pattern of Prism-PET of embodiments of the present disclosure. FIG. 17 shows that experimental results of several examples of Compton events absorbed in adjacent crystals in a Prism-PET module of the present disclosure vs. a module with a flat glass light guide.

The light sharing pattern in the glass light guide module is random, making it difficult (and in most cases, impossible) to decompose the detected energies into the constituent energies of the scattered photon and recoil electron. Due to the right triangular prism geometry, the light sharing pattern is deterministic in the Prism-PET module, making it practical to decompose the event into its constituent energies based on the known light sharing ratios between crystals.

Accordingly, a particle detector is provided that includes a scintillator array comprising a plurality of scintillator crystals; a plurality of detectors provided on a bottom end of the scintillator array; a plurality of prismatoids provided on a top end of the scintillator array; and at least one processor in operative communication with the plurality of detectors. The at least one processor comprises a plurality of supervised machine learning algorithms, including convolutional and regressive networks, configured to perform 3D gamma ray localization of at least one interaction site within at least one scintillator crystal of the plurality of scintillator crystals. The at least one processor is configured to recover at least one Compton event scattering among the plurality of scintillator crystals, and localize the at least one Compton event at a scintillator level based on 3D gamma ray localization. The at least one processor is further configured to determine a scatter angle based on at least one Compton event and DOI information. The at least one processor is further configured to localize at least one Compton event based on decomposed energies of at least two interactions absorbed in the plurality of scintillator crystals, with the decomposed energies based on at least one light sharing pattern and the at least one light sharing pattern being based on positions of the plurality of scintillator crystals relative to the plurality of detectors and the plurality of prismatoids.

According to embodiments of the present disclosure, the at least one light sharing pattern is mapped based on light sharing ratios between scintillator crystals of a same prismatoid; the light sharing ratios are based on a predefined geometry of at least one prismatoid of the plurality of prismatoids; the mapping is based on measured photoelectric events, decomposed energies of at least one primary interaction and at least one secondary interaction, and the at least one primary interaction is based on electron recoil and the at least one secondary interaction is based on gamma ray scattering, with the light sharing pattern being deterministic.

Accordingly, a cost-effective and practical method for achieving high spatial and DOI resolution in multicrystal single-ended readout detector modules is provided without introducing edge and corner artifacts. Embodiments of the present disclosure can be used to enable depth-encoding in clinical whole-body and total-body PET scanners [23] without increasing cost (prismatoid light guide array comprises less than 10% of the total cost of each Prism-PET module) and power consumption, while improving spatial resolution (via 9-to-1 coupling of, for example, 2×2×20 mm³ crystals to 6×6 mm² readout pixels), sensitivity (via intercrystal Compton scatter recovery), and timing resolution (via DOI-correction of timing jitter). For small ring-diameter brain imaging, the 9-to-1 coupling ratio enables sub-millimeter spatial resolution, while extending axial field-of-view to about double that of whole-body PET scanners enables the same geometric sensitivity gain as the Explorer total-body PET scanner (FIG. 15) [8, 23-26]. In addition, having 2.5 mm DOI resolution greatly mitigates parallax error and potentially enables achieving ~100 ps coincidence time resolution via DOI-correction [8], which would enable even higher sensitivity and spatial resolution [24-26]. These benefits yield a practical, cost-effective, and power efficient approach to achieving both high spatial resolution and high sensitivity at relatively low dose for quantitative in vivo functional and molecular imaging of many human body organs, including important structures of the brain that have not been resolvable with existing PET scanners such as the raphe nuclei, cholinergic basal forebrain nuclei, Locus coeruleus and hypothalamic nuclei, all of which are thought to play crucial roles in basic physiology as well as in the pathophysiology of common neurodegenerative and psychiatric disorders [26-30]. The ability to visualize and quantitate these and similar targets has the potential to revolutionize molecular imaging in both the clinical and research arenas, providing hitherto unavailable tools for early diagnosis and basic research in oncology and brain disorders.

Another advantage of embodiments of the present disclosure is the ability to more accurately identify the initial interaction site of Compton scatter events, further improving spatial resolution and sensitivity (FIGS. 16-17). Traditionally, Compton detection has been performed using multiple detector layers, but a recent paper outlined the criteria for localizing and decomposing Compton interactions using single-ended readout, citing high resolution DOI readout as a key feature for Compton scatter recovery [31]. A uniform light guide is not optimal for this task because the SiPM pattern of individual events is random, whereas our Prism-PET modules create a deterministic light sharing pattern regardless of the interaction location inside the primary scintillator column (FIGS. 1-4 and 14). Notably, Prism-PET enables the decomposition of side-by-side scattered photon and recoil electron events, which are the most probable and most difficult to analyze scattering events, into their constituent energies, spatial location, and DOI. Compton scatter recovery is especially critical to retain high sensitivity in detector modules with small scintillator crystals since the scattered photon is more likely to be absorbed in a different crystal from the primary interaction site as crystal size decreases [32].

Embodiments of the present disclosure provide a Prism-PET detector module which is a true single-ended analogy of a dual-ended depth-encoding readout using efficient 180° light bending reflectors for enhanced light sharing. A 2.5 mm FWHM DOI resolution is achieved and up to 9-to-1 scintillator to SiPM coupling for high spatial resolution while directly coupling the crystal array to the SiPM pixels to minimize light leakage and retain high photon detection efficiency, which is required for good timing resolution. The top side reflector is comprised of an optimized pattern of segmented prismatoid light guides for efficient redirection of scintillation photon paths from the primary crystal to selected nearest-neighboring SiPMs, thus mimicking very closely the operation of dual-ended readout detectors. This creates an anisotropic and deterministic pattern of signal that can be used to decompose a side-by-side Compton scattering events into their constituent energy and DOI information for the purpose of scatter recovery. Thus, high and uniform spatial resolution are achieved (9-to-1 coupling of ~1 mm crystals; absence of edge and corner artifacts due to enhanced light sharing; reduced spatial blur due to Compton-scattered photons via scatter recovery), high sensitivity is achieved (20-mm thick detectors, and intercrystal Compton scatter recovery), and good energy and timing resolutions are achieved (especially after applying DOI-correction) in compact systems (DOI encoding eliminates parallax error and permits smaller ring-diameter). With these unique combinations of features, cost-effective and compact TOF-DOI-Compton PET scanners could be developed based upon Prism-PET modules for small animal and human organ-specific functional and molecular imaging.

While the invention has been shown and described with reference to certain aspects thereof, it will be understood by those skilled in the art that various changes in form and details may be made therein without departing from the spirit and scope of the present invention as defined by the appended claims and equivalents thereof. No recitation of any claim set forth below is to be construed as a means plus function element without express use of "means for" or "step for."

REFERENCES

[1] Mankoff D A, Farwell M D, Clark A S, Pryma D A. Making molecular imaging a clinical tool for precision oncology: a review. JAMA Oncol. 2017; 3:695-701.

[2] Slifstein M, Abi-Dargham A. Recent developments in molecular brain imaging of neuropsychiatric disorders. Semin Nucl Med. 2017; 47:54-63.

[3] Van Sluis J, De Jong J, Schaar J, et al. Performance characteristics of the digital biograph vision PET/CT system. J Nucl Med. 2019; 60:1031-1036.

[4] Moses W W. Fundamental limits of spatial resolution in PET. Nucl Instr and Meth A. 2011; 648:5236-5240.

[5] Miyaoka R S, Lewellen T K, Yu H, McDaniel D L. Design of a depth of interaction (DOI) PET detector module. IEEE Trans Nucl Sci. 1998; 45:1069-1073.

[6] Stickel J R, Cherry S R. High-resolution PET detector design: modelling components of intrinsic spatial resolution. Phys Med Biol. 2005; 50:179-195.

[7] Seifert S, Schaart D R. Improving the time resolution of TOF-PET detectors by double-sided readout. IEEE Trans Nucl Sci. 2015; 62:3-11.

[8] Pizzichemi M, Polesel A, Stringhini G, et al. On light sharing TOF-PET modules with 3 mm depth of interaction and 157 ps FWHM coincidence time resolution. Phys Med Biol. 2019; 64:155008.

[9] Yang Y, Wu Y, Qi J, et al. A prototype PET scanner with DOI-encoding detectors. J Nucl Med. 2008; 49:1132-40.

[10] Kuang Z, Wang X, Fu X, et al. Dual-ended readout small animal PET detector by using 0.5 mm pixelated LYSO crystal arrays and SiPMs. Nucl Instr and Meth A. 2019; 917:1-8.

[11] Abreu M C, Aguiar J D, Almeida F G, et al. Design and evaluation of the clear-PEM scanner for positron emission mammography. IEEE Trans Nucl Sci. 2006; 53:71-77.

[12] Du J, Yang Y, Bal X, et al. Characterization of large-area SiPM array for PET applications. IEEE Trans Nucl Sci. 2016; 63:8-16.

[13] Schmand M, Eriksson L, Casey M E, et al. Performance results of a new DOI detector block for a high resolution PET-LSO research tomograph HRRT. IEEE Trans Nucl Sci. 1998; 45:3000-3006.

[14] Seidel J, Vaquero J J, Siegel S, et al. Depth identification accuracy of a three layer phoswich PET detector module. IEEE Trans Nucl Sci. 1999; 46:485-490.

[15] Gonzalez-Montoro A, Aguilar A, Canizares G, et al. Performance study of a large monolithic LYSO PET detector with accurate photon DOI using retroreflector layers. IEEE Trans Rad Plasma Med Sc. 2017; 1:229-237.

[16] Ito M, Lee M S, Lee J S. Continuous depth-of-interaction measurement in a single-layer pixelated crystal array using a single-ended readout. Phys Med Biol. 2013; 58:1269-1282.

[17] Kuang Z, Yang Q, Wang X, et al. A depth-encoding PET detector that uses light sharing and single-ended readout with silicon photomultipliers. Phys Med Biol. 2018; 63:045009.

[18] Pizzichemi M, Stringhini G, Niknejad T, et al. A new method for depth of interaction determination in PET detectors. Phys Med Biol. 2016; 61:4679-4698.

[19] Niknejad T, Pizzichemi M, Stringhini G, et al. Development of high-resolution detector module with depth of interaction identification for positron emission tomography. Nucl Instr and Meth A. 2017; 845:684-688.
[20] Stringhini G, Pizzichemi M, Ghezzi A, et al. Development of a high resolution module for PET scanners. J Instrum. 2017; 12:C02073-C02073.
[21] Kuang Z, Wang X, Li C, et al. Performance of a high-resolution depth encoding PET detector using barium sulfate reflector. Phys Med Biol. 2017; 62:5945-5958.
[22] Otte A N, Barral J, Dolgoshein B, et al. A test of silicon photomultipliers as readout for PET. Nucl Instr and Meth A. 2005; 545:705-715.
[23] Badawi R D, Shi H, Hu P, et al. First human imaging studies with the explorer total-body PET scanner. J Nucl Med. 2019; 60:299-303.
[24] Surti S. Update on time-of-flight PET imaging. J Nucl Med. 2015; 56:98-105.
[25] Reddin J S, Scheuermann J S, Bharkhada D, et al. Performance evaluation of the SiPM-based Siemens Biograph Vision PET/CT system. In: Conference Record of the 2018 IEEE Nuclear Science Symposium and Medical Imaging Conference. Sydney, AU: IEEE; 2018.
[26] Gong K, Majewski S, Kinahan P E, et al. Designing a compact high performance brain PET scanner—simulation study. Phys Med Biol. 2016; 61:3681-3697.
[27] Hornung J P. The human raphe nuclei and the serotonergic system. J Chem. Neuroanat. 2003; 26:331-343.
[28] Mufson E J, Ginsberg S D, Ikonomovic M D, DeKosky S T. Human cholinergic basal forebrain: Chemoanatomy and neurologic dysfunction. J Chem Neuroanat. 2003; 26:233-242.
[29] Betts M J, Kirilina E, Otaduy M C G, et al. Locus coeruleus imaging as a biomarker for noradrenergic dysfunction in neurodegenerative diseases. Brain. 2019; 142:2558-2571.
[30] Barbosa D A, de Oliveira-Souza R, Santo F M, et al. The hypothalamus at the crossroads of psychopathology and neurosurgery. Neurosurg Focus. 2017; 43:1-11.
[31] Makek M, Bosnar D, Pavelie L. Scintillator pixel detectors for measurement of Compton scattering. Condens Matter. 2019; 4:24.
[32] Hsu D F, Freese D L, Innes D R, Levin C S. Intercrystal scatter studies for a 1 mm³ resolution clinical PET system prototype. Phys Med Biol. 2019; 64:095024.

What is claimed is:

1. A particle detector, comprising:
a scintillator array comprising a plurality of scintillator crystals;
a plurality of detectors provided on a first end of the scintillator array;
a plurality of prismatoids provided on a second end of the scintillator array; and
at least one processor in operative communication with the plurality of detectors,
wherein the at least one processor comprises a plurality of supervised machine learning algorithms configured to perform three dimensional (3D) gamma ray localization of at least one interaction site within at least one scintillator crystal of the plurality of scintillator crystals based on a light sharing pattern between scintillator crystals associated with the same prismatoid, where the light sharing pattern is dependent on a predefined geometry of the same prismatoid.

2. The particle detector of claim 1, wherein the at least one processor is further configured to recover at least one Compton event scattering among the plurality of scintillator crystals, and localize the at least one Compton event at a scintillator level based on the 3D gamma ray localization.

3. The particle detector of claim 1, wherein the at least one processor is further configured to determine a scatter angle based on at least one Compton event and depth of interaction (DOI) information.

4. The particle detector of claim 1, wherein the at least one processor is further configured to localize at least one Compton event based on decomposed energies of at least two interactions absorbed in the plurality of scintillator crystals.

5. The particle detector of claim 4, wherein the decomposed energies are based on at least one light sharing pattern.

6. The particle detector of claim 5, wherein the at least one light sharing pattern is based on positions of the plurality of scintillator crystals relative to the plurality of detectors and the plurality of prismatoids.

7. The particle detector of claim 5, wherein the at least one light sharing pattern is mapped based on light sharing ratios between scintillator crystals of a same prismatoid.

8. The particle detector of claim 7, wherein the light sharing ratios are based on a predefined geometry of the same prismatoid.

9. The particle detector of claim 7, wherein the mapping is based on measured photoelectric events, decomposed energies of at least one primary interaction and at least one secondary interaction, and
wherein the at least one primary interaction is based on electron recoil and the at least one secondary interaction is based on gamma ray scattering.

* * * * *